United States Patent
Shih et al.

(10) Patent No.: US 9,283,322 B2
(45) Date of Patent: Mar. 15, 2016

(54) DRUG-DELIVERY PUMP WITH DYNAMIC, ADAPTIVE CONTROL

(71) Applicants: Jason Shih, Yorba Linda, CA (US); Jeffrey Brennan, Los Angeles, CA (US); Fukang Jiang, Pasadena, CA (US); Sean Caffey, Pasadena, CA (US)

(72) Inventors: Jason Shih, Yorba Linda, CA (US); Jeffrey Brennan, Los Angeles, CA (US); Fukang Jiang, Pasadena, CA (US); Sean Caffey, Pasadena, CA (US)

(73) Assignee: MiniPumps, LLC, Pasadena, CA (US)

(*) Notice: Subject to any disclaimer, the term of this patent is extended or adjusted under 35 U.S.C. 154(b) by 285 days.

(21) Appl. No.: 13/939,593

(22) Filed: Jul. 11, 2013

(65) Prior Publication Data

US 2014/0074058 A1  Mar. 13, 2014

Related U.S. Application Data

(60) Division of application No. 12/858,808, filed on Aug. 18, 2010, which is a continuation-in-part of application No. 12/463,265, filed on May 8, 2009.

(60) Provisional application No. 61/051,422, filed on May 8, 2008, provisional application No. 61/197,751, filed on Oct. 30, 2008, provisional application No. 61/197,769, filed on Oct. 30, 2008, provisional application No. 61/198,131, filed on Nov. 3, 2008, provisional application No. 61/198,090, filed on Nov. 3, 2008, provisional application No. 61/234,742, filed on Aug. 18, 2009.

(51) Int. Cl.
| | | |
|---|---|---|
| *A61M 5/168* | (2006.01) | |
| *A61M 5/142* | (2006.01) | |
| *A61M 5/172* | (2006.01) | |
| *A61F 9/00* | (2006.01) | |

(Continued)

(52) U.S. Cl.
CPC .......... *A61M 5/16831* (2013.01); *A61F 9/0017* (2013.01); *A61M 5/14276* (2013.01); *A61M 5/16804* (2013.01); *A61M 5/172* (2013.01); *G06F 19/3468* (2013.01); *A61M 5/148* (2013.01); *A61M 5/14244* (2013.01); *A61M 5/16854* (2013.01); *A61M 31/002* (2013.01); *A61M 2005/14204* (2013.01); *A61M 2205/3331* (2013.01); *A61M 2205/3368* (2013.01); *A61M 2210/0612* (2013.01); *A61M 2210/0693* (2013.01)

(58) Field of Classification Search
CPC ........ A61M 5/16831–5/1723; A61M 5/14244; A61M 5/14276; A61M 5/148; A61M 5/172; A61M 5/16804; A61M 5/16877; A61M 5/16854; A61M 2005/14204; A61M 2205/52; A61M 2205/6018; A61M 2205/50; A61M 2205/3331; A61M 2210/0612; A61M 2210/0693; A61F 9/0017; A61F 19/3468
See application file for complete search history.

(56) References Cited

U.S. PATENT DOCUMENTS

| | | |
|---|---|---|
| 2,445,477 A | 7/1948 | Folkman |
| 3,175,558 A | 3/1965 | Caillonette et al. |

(Continued)

FOREIGN PATENT DOCUMENTS

| | | |
|---|---|---|
| CN | 1321096 A | 11/2001 |
| CN | 102576385 A | 7/2012 |

(Continued)

OTHER PUBLICATIONS

Examination Report in European Patent Application No. 07753177.0, mailed on Jan. 29, 2009, 6 pages.

(Continued)

*Primary Examiner* — Bhisma Mehta
*Assistant Examiner* — Jenna Zhang
(74) *Attorney, Agent, or Firm* — Morgan, Lewis & Bockius LLP

(57) ABSTRACT

In various embodiments, actuation of a drug-delivery pump is controlled based on a change in a condition of the pump.

9 Claims, 8 Drawing Sheets

(51) Int. Cl.
  *G06F 19/00* (2011.01)
  *A61M 5/148* (2006.01)
  *A61M 31/00* (2006.01)

(56) References Cited

U.S. PATENT DOCUMENTS

| | | | |
|---|---|---|---|
| 3,731,681 A | 5/1973 | Blackshear et al. | |
| 3,760,805 A | 9/1973 | Higuchi | |
| 3,894,538 A | 7/1975 | Richter | |
| 3,916,899 A | 11/1975 | Theeuwes et al. | |
| 3,977,404 A | 8/1976 | Theeuwes | |
| 4,140,121 A | 2/1979 | Kuhl et al. | |
| 4,140,122 A | 2/1979 | Kuhl et al. | |
| 4,150,673 A | 4/1979 | Watt | |
| 4,164,560 A | 8/1979 | Folkman et al. | |
| 4,180,375 A | 12/1979 | Magnussen | |
| 4,203,441 A | 5/1980 | Theeuwes | |
| 4,237,881 A | 12/1980 | Beigler et al. | |
| 4,300,554 A | 11/1981 | Hessberg et al. | |
| 4,373,527 A | 2/1983 | Fischell | |
| 4,543,088 A | 9/1985 | Bootman et al. | |
| 4,553,973 A | 11/1985 | Edgren | |
| 4,692,145 A | 9/1987 | Weyant | |
| 4,738,657 A | 4/1988 | Hancock et al. | |
| 4,751,926 A | 6/1988 | Sasaki | |
| 4,760,837 A | 8/1988 | Petit | |
| 4,781,675 A | 11/1988 | White | |
| 4,781,695 A | 11/1988 | Dalton | |
| 4,838,887 A | 6/1989 | Idriss | |
| 4,853,224 A | 8/1989 | Wong | |
| 4,886,499 A | 12/1989 | Cirelli et al. | |
| 4,886,514 A | 12/1989 | Maget | |
| 4,888,176 A | 12/1989 | Langer et al. | |
| 4,902,278 A | 2/1990 | Maget et al. | |
| 4,923,457 A | 5/1990 | Ellingsen | |
| 4,944,659 A | 7/1990 | Labbe et al. | |
| 4,959,217 A | 9/1990 | Sanders et al. | |
| 4,969,874 A | 11/1990 | Michel et al. | |
| 5,062,834 A | 11/1991 | Gross et al. | |
| 5,066,276 A | 11/1991 | Wang | |
| 5,067,491 A | 11/1991 | Taylor et al. | |
| 5,090,963 A | 2/1992 | Gross et al. | |
| 5,108,372 A * | 4/1992 | Swenson | A61M 5/16886 604/113 |
| 5,135,498 A | 8/1992 | Kam et al. | |
| 5,135,499 A | 8/1992 | Tafani et al. | |
| 5,147,647 A | 9/1992 | Darougar | |
| 5,163,909 A | 11/1992 | Stewart | |
| 5,164,188 A | 11/1992 | Wong | |
| 5,171,213 A | 12/1992 | Price, Jr. | |
| 5,178,604 A | 1/1993 | Baerveldt et al. | |
| 5,207,227 A * | 5/1993 | Powers | A61B 5/028 600/488 |
| 5,213,568 A | 5/1993 | Lattin et al. | |
| 5,242,406 A | 9/1993 | Gross et al. | |
| 5,242,408 A | 9/1993 | Jhuboo et al. | |
| 5,252,192 A | 10/1993 | Ludwig | |
| 5,279,607 A | 1/1994 | Schentag et al. | |
| 5,318,540 A | 6/1994 | Athayde et al. | |
| 5,318,557 A | 6/1994 | Gross | |
| 5,354,264 A | 10/1994 | Bae et al. | |
| 5,368,571 A | 11/1994 | Horres, Jr. | |
| 5,399,166 A | 3/1995 | Laing | |
| 5,407,441 A | 4/1995 | Greenbaum | |
| 5,425,716 A | 6/1995 | Kawasaki et al. | |
| 5,443,505 A | 8/1995 | Wong et al. | |
| 5,458,095 A | 10/1995 | Post et al. | |
| 5,462,739 A | 10/1995 | Dan et al. | |
| 5,472,436 A | 12/1995 | Fremstad | |
| 5,474,527 A | 12/1995 | Bettinger | |
| 5,476,445 A | 12/1995 | Baerveldt et al. | |
| 5,505,697 A | 4/1996 | McKinnon et al. | |
| 5,527,288 A | 6/1996 | Gross et al. | |
| 5,553,741 A | 9/1996 | Sancoff et al. | |
| 5,616,219 A | 4/1997 | Patterson | |
| 5,629,008 A | 5/1997 | Lee | |
| 5,676,651 A | 10/1997 | Larson, Jr. et al. | |
| 5,697,153 A | 12/1997 | Saaski et al. | |
| 5,704,520 A | 1/1998 | Gross | |
| 5,707,499 A | 1/1998 | Joshi et al. | |
| 5,713,857 A | 2/1998 | Grimard et al. | |
| 5,725,017 A | 3/1998 | Elsberry et al. | |
| 5,725,493 A | 3/1998 | Avery et al. | |
| 5,741,275 A | 4/1998 | Wyssmann | |
| 5,782,799 A | 7/1998 | Jacobsen et al. | |
| 5,785,688 A | 7/1998 | Joshi et al. | |
| 5,788,682 A * | 8/1998 | Maget | A61F 13/00063 604/290 |
| 5,798,114 A | 8/1998 | Elsberry et al. | |
| 5,798,115 A | 8/1998 | Santerre et al. | |
| 5,800,420 A * | 9/1998 | Gross | A61K 9/0021 204/280 |
| 5,824,072 A | 10/1998 | Wong | |
| 5,830,173 A | 11/1998 | Avery et al. | |
| 5,836,935 A | 11/1998 | Ashton et al. | |
| 5,868,697 A | 2/1999 | Richter et al. | |
| 5,891,097 A | 4/1999 | Saito et al. | |
| 5,904,144 A | 5/1999 | Hammang et al. | |
| 5,951,538 A | 9/1999 | Joshi et al. | |
| 5,989,579 A | 11/1999 | Darougar et al. | |
| 5,993,374 A | 11/1999 | Kick | |
| 5,993,414 A | 11/1999 | Haller | |
| 6,048,328 A | 4/2000 | Haller et al. | |
| 6,129,696 A | 10/2000 | Sibalis | |
| 6,144,106 A | 11/2000 | Bearinger et al. | |
| 6,203,523 B1 | 3/2001 | Haller et al. | |
| 6,240,962 B1 | 6/2001 | Tai et al. | |
| 6,251,090 B1 | 6/2001 | Avery et al. | |
| 6,254,586 B1 | 7/2001 | Mann et al. | |
| 6,264,971 B1 | 7/2001 | Darougar et al. | |
| 6,281,192 B1 | 8/2001 | Leahy et al. | |
| 6,287,295 B1 | 9/2001 | Chen et al. | |
| 6,370,970 B1 | 4/2002 | Hosokawa et al. | |
| 6,375,972 B1 | 4/2002 | Guo et al. | |
| 6,390,791 B1 | 5/2002 | Maillefer et al. | |
| 6,390,797 B1 | 5/2002 | Myers | |
| 6,408,878 B2 | 6/2002 | Unger et al. | |
| 6,413,238 B1 * | 7/2002 | Maget | A61M 5/14526 604/132 |
| 6,416,777 B1 | 7/2002 | Yaacobi | |
| 6,458,102 B1 | 10/2002 | Mann et al. | |
| 6,491,684 B1 | 12/2002 | Joshi et al. | |
| 6,520,936 B1 | 2/2003 | Mann | |
| 6,527,744 B1 | 3/2003 | Kriesel et al. | |
| 6,537,268 B1 | 3/2003 | Gibson et al. | |
| 6,589,205 B1 | 7/2003 | Meadows | |
| 6,669,950 B2 | 12/2003 | Yaacobi | |
| 6,697,694 B2 | 2/2004 | Mogensen | |
| 6,699,394 B2 | 3/2004 | Tai et al. | |
| 6,713,081 B2 | 3/2004 | Robinson et al. | |
| 6,719,750 B2 | 4/2004 | Varner et al. | |
| 6,817,252 B2 | 11/2004 | Wiklund et al. | |
| 6,852,097 B1 | 2/2005 | Fulton, III | |
| 6,852,106 B2 | 2/2005 | Watson et al. | |
| 6,899,137 B2 | 5/2005 | Unger et al. | |
| 6,948,918 B2 | 9/2005 | Hansen | |
| 6,955,670 B2 | 10/2005 | Martin et al. | |
| 6,973,718 B2 * | 12/2005 | Sheppard, Jr. | A61K 9/0009 29/841 |
| 7,070,577 B1 | 7/2006 | Haller et al. | |
| 7,225,683 B2 | 6/2007 | Harnett et al. | |
| 7,276,050 B2 | 10/2007 | Franklin | |
| 7,351,303 B2 | 4/2008 | Liu et al. | |
| 7,429,258 B2 | 9/2008 | Angel et al. | |
| 7,470,267 B2 | 12/2008 | Joshi et al. | |
| 7,517,440 B2 | 4/2009 | Anex et al. | |
| 7,524,304 B2 | 4/2009 | Genosar | |
| 7,537,590 B2 | 5/2009 | Santini, Jr. et al. | |
| 7,544,190 B2 | 6/2009 | Pickup et al. | |
| 7,606,615 B2 | 10/2009 | Makower et al. | |
| 7,766,873 B2 | 8/2010 | Moberg et al. | |
| 7,828,771 B2 | 11/2010 | Chiang et al. | |
| 7,867,203 B2 | 1/2011 | Rosenberg et al. | |
| 7,887,508 B2 | 2/2011 | Meng et al. | |

(56) References Cited

U.S. PATENT DOCUMENTS

| | | |
|---|---|---|
| 7,931,643 B2 | 4/2011 | Olsen et al. |
| 8,147,447 B2 | 4/2012 | Sundar et al. |
| 8,231,608 B2 | 7/2012 | Pang et al. |
| 8,231,609 B2 | 7/2012 | Pang et al. |
| 8,285,328 B2 | 10/2012 | Caffey et al. |
| 8,486,278 B2 | 7/2013 | Pang et al. |
| 8,585,648 B2 | 11/2013 | Caffey |
| 8,920,376 B2 | 12/2014 | Caffey et al. |
| 8,939,930 B2 | 1/2015 | Li et al. |
| 2002/0016569 A1 | 2/2002 | Critchlow et al. |
| 2002/0026176 A1 | 2/2002 | Varner et al. |
| 2002/0040208 A1 | 4/2002 | Flaherty et al. |
| 2002/0103412 A1 | 8/2002 | Trimmer |
| 2002/0156462 A1 | 10/2002 | Stultz |
| 2002/0188282 A1 | 12/2002 | Greenberg |
| 2003/0014014 A1 | 1/2003 | Nitzan |
| 2003/0014036 A1 | 1/2003 | Varner et al. |
| 2003/0064088 A1 | 4/2003 | Carvalho et al. |
| 2003/0069560 A1 | 4/2003 | Adamis et al. |
| 2003/0141618 A1 | 7/2003 | Braithwaite et al. |
| 2004/0028655 A1 | 2/2004 | Nelson et al. |
| 2004/0096410 A1 | 5/2004 | Maley et al. |
| 2004/0100528 A1 | 5/2004 | Howkins et al. |
| 2004/0106914 A1 | 6/2004 | Coppeta et al. |
| 2004/0126253 A1 | 7/2004 | Gray et al. |
| 2004/0143221 A1 | 7/2004 | Shadduck |
| 2004/0175410 A1 | 9/2004 | Ashton et al. |
| 2004/0188648 A1 | 9/2004 | Xie et al. |
| 2004/0199130 A1 | 10/2004 | Chornenky et al. |
| 2004/0208910 A1 | 10/2004 | Ashton et al. |
| 2004/0228734 A1 | 11/2004 | Jeon et al. |
| 2005/0010175 A1 | 1/2005 | Beedon et al. |
| 2005/0059926 A1* | 3/2005 | Sage, Jr. ............... A61M 5/168 604/65 |
| 2005/0065500 A1 | 3/2005 | Couvillon et al. |
| 2005/0076242 A1 | 4/2005 | Breuer |
| 2005/0096707 A1 | 5/2005 | Hill et al. |
| 2005/0106225 A1 | 5/2005 | Massengale et al. |
| 2005/0175708 A1 | 8/2005 | Carrasquillo et al. |
| 2005/0187515 A1 | 8/2005 | Varrichio et al. |
| 2005/0208103 A1 | 9/2005 | Adamis et al. |
| 2005/0209562 A1 | 9/2005 | Kim |
| 2005/0214129 A1 | 9/2005 | Greene et al. |
| 2005/0247558 A1* | 11/2005 | Anex ............... A61M 5/14248 204/275.1 |
| 2006/0004330 A1* | 1/2006 | Carlisle ............... A61M 5/1408 604/246 |
| 2006/0012280 A1 | 1/2006 | Kang et al. |
| 2006/0014793 A1 | 1/2006 | Nakamura et al. |
| 2006/0047538 A1 | 3/2006 | Condurso et al. |
| 2006/0052666 A1 | 3/2006 | Kumar et al. |
| 2006/0052768 A1 | 3/2006 | Joshi et al. |
| 2006/0075016 A1 | 4/2006 | Kanayama et al. |
| 2006/0089619 A1 | 4/2006 | Ginggen |
| 2006/0116641 A1 | 6/2006 | Gordon et al. |
| 2006/0167435 A1 | 7/2006 | Adamis et al. |
| 2006/0178655 A1 | 8/2006 | Santini et al. |
| 2006/0200073 A1 | 9/2006 | Radmer et al. |
| 2006/0200097 A1 | 9/2006 | Humayun et al. |
| 2006/0258994 A1 | 11/2006 | Avery |
| 2006/0259015 A1 | 11/2006 | Steinbach |
| 2006/0271020 A1 | 11/2006 | Huang et al. |
| 2007/0021735 A1 | 1/2007 | Bhavaraju et al. |
| 2007/0060870 A1 | 3/2007 | Tolle et al. |
| 2007/0066939 A1 | 3/2007 | Krulevitch et al. |
| 2007/0084765 A1 | 4/2007 | Tse |
| 2007/0093752 A1 | 4/2007 | Zhao et al. |
| 2007/0106199 A1 | 5/2007 | Krivoy et al. |
| 2007/0106218 A1 | 5/2007 | Yodfat et al. |
| 2007/0106557 A1 | 5/2007 | Varghese |
| 2007/0112328 A1 | 5/2007 | Steinbach et al. |
| 2007/0118066 A1 | 5/2007 | Pinchuk et al. |
| 2007/0173900 A1 | 7/2007 | Siegel et al. |
| 2007/0191770 A1 | 8/2007 | Moberg et al. |
| 2007/0228071 A1* | 10/2007 | Kamen ............... G05D 7/0647 222/52 |
| 2007/0255233 A1 | 11/2007 | Haase |
| 2007/0255235 A1 | 11/2007 | Olsen et al. |
| 2007/0255250 A1 | 11/2007 | Moberg et al. |
| 2007/0255261 A1 | 11/2007 | Haase |
| 2007/0269487 A1 | 11/2007 | de Juan et al. |
| 2007/0275384 A1 | 11/2007 | Leppert et al. |
| 2008/0015494 A1 | 1/2008 | Santini et al. |
| 2008/0022789 A1 | 1/2008 | Okuno et al. |
| 2008/0033255 A1 | 2/2008 | Essenpreis et al. |
| 2008/0039768 A1 | 2/2008 | Francis |
| 2008/0039792 A1* | 2/2008 | Meng ............... A61K 9/0024 604/114 |
| 2008/0097412 A1 | 4/2008 | Shuros et al. |
| 2008/0102119 A1 | 5/2008 | Grovender et al. |
| 2008/0119707 A1 | 5/2008 | Stafford |
| 2008/0125702 A1 | 5/2008 | Blischak et al. |
| 2008/0170936 A1 | 7/2008 | Den Toonder et al. |
| 2008/0181930 A1 | 7/2008 | Rodstrom et al. |
| 2008/0194053 A1 | 8/2008 | Huang |
| 2008/0234637 A1 | 9/2008 | McConnell et al. |
| 2008/0243071 A1 | 10/2008 | Quijano et al. |
| 2008/0269664 A1 | 10/2008 | Trovato et al. |
| 2008/0275384 A1 | 11/2008 | Mastrototaro |
| 2008/0312584 A1 | 12/2008 | Montgomery et al. |
| 2009/0028824 A1 | 1/2009 | Chiang et al. |
| 2009/0041624 A1 | 2/2009 | Hochmuth et al. |
| 2009/0112188 A1 | 4/2009 | Santini, Jr. et al. |
| 2009/0188576 A1 | 7/2009 | Kang et al. |
| 2009/0192493 A1 | 7/2009 | Meng et al. |
| 2009/0205399 A1 | 8/2009 | Sun et al. |
| 2009/0227855 A1 | 9/2009 | Hill et al. |
| 2009/0234366 A1 | 9/2009 | Tsai et al. |
| 2009/0234594 A1 | 9/2009 | Carlisle et al. |
| 2009/0240215 A1 | 9/2009 | Humayun et al. |
| 2009/0259176 A1 | 10/2009 | Yairi |
| 2009/0281528 A1 | 11/2009 | Grovender et al. |
| 2009/0306585 A1 | 12/2009 | Pang et al. |
| 2009/0306594 A1 | 12/2009 | Pang et al. |
| 2009/0306595 A1 | 12/2009 | Shih et al. |
| 2009/0306633 A1 | 12/2009 | Trovato et al. |
| 2009/0308752 A1 | 12/2009 | Evans et al. |
| 2009/0311133 A1 | 12/2009 | Pang et al. |
| 2009/0312742 A1 | 12/2009 | Pang et al. |
| 2010/0004639 A1 | 1/2010 | Pang et al. |
| 2010/0030550 A1 | 2/2010 | Travieso et al. |
| 2010/0049120 A1 | 2/2010 | Dijksman et al. |
| 2010/0101670 A1 | 4/2010 | Juncker et al. |
| 2010/0114002 A1 | 5/2010 | O'Mahony et al. |
| 2010/0143448 A1 | 6/2010 | Nisato et al. |
| 2010/0222769 A1 | 9/2010 | Meng et al. |
| 2010/0234805 A1 | 9/2010 | Kaufmann et al. |
| 2010/0241103 A1 | 9/2010 | Kraft et al. |
| 2010/0292557 A1* | 11/2010 | Pesach ............... A61B 5/14532 600/365 |
| 2010/0292635 A1 | 11/2010 | Sundar |
| 2010/0305550 A1 | 12/2010 | Meng et al. |
| 2011/0144586 A1 | 6/2011 | Michaud et al. |
| 2011/0184342 A1 | 7/2011 | Pesach et al. |
| 2011/0190702 A1 | 8/2011 | Stumber |
| 2011/0202032 A1 | 8/2011 | Shih et al. |
| 2011/0270188 A1 | 11/2011 | Caffey et al. |
| 2011/0275410 A1 | 11/2011 | Caffey et al. |
| 2011/0275987 A1 | 11/2011 | Caffey et al. |
| 2012/0041427 A1 | 2/2012 | Caffey et al. |
| 2012/0046651 A1 | 2/2012 | Beyer et al. |
| 2012/0222488 A1 | 9/2012 | Slocum |
| 2012/0283691 A1 | 11/2012 | Barnes et al. |
| 2013/0178792 A1 | 7/2013 | Li |
| 2013/0178826 A1 | 7/2013 | Li |
| 2013/0184640 A1 | 7/2013 | Li |
| 2013/0184641 A1 | 7/2013 | Li |
| 2013/0276974 A1 | 10/2013 | Pang et al. |
| 2013/0289497 A1 | 10/2013 | Humayun et al. |
| 2013/0296810 A1 | 11/2013 | Humayun et al. |
| 2014/0088554 A1 | 3/2014 | Li et al. |

(56) References Cited

U.S. PATENT DOCUMENTS

| | | |
|---|---|---|
| 2014/0088555 A1 | 3/2014 | Li et al. |
| 2014/0094770 A1 | 4/2014 | Li et al. |
| 2014/0094771 A1 | 4/2014 | Li et al. |

FOREIGN PATENT DOCUMENTS

| | | |
|---|---|---|
| CN | 103108665 A | 5/2013 |
| CN | 102202719 B | 11/2014 |
| CN | 104353150 A | 2/2015 |
| DE | 3915708 A1 | 2/1990 |
| DE | 3915708 A1 | 2/1990 |
| DE | 4436540 A1 | 4/1996 |
| DE | 102004036358 A1 | 2/2006 |
| EP | 209677 A1 | 1/1987 |
| EP | 251680 A2 | 1/1988 |
| EP | 0251680 A2 | 1/1988 |
| EP | 646381 A1 | 4/1995 |
| EP | 815896 A2 | 1/1998 |
| EP | 1649884 A1 | 4/2006 |
| EP | 1841491 A1 | 10/2007 |
| EP | 2467797 A1 | 6/2012 |
| EP | 2560703 A2 | 2/2013 |
| EP | 2780055 A2 | 9/2014 |
| EP | 2320989 B1 | 3/2015 |
| GB | 1345764 A | 2/1974 |
| GB | 1345764 A | 2/1974 |
| GB | 1452104 A | 10/1976 |
| IE | 38474 L | 6/1973 |
| IE | 38474 B1 | 3/1978 |
| JP | 2003-299732 A | 10/2003 |
| WO | 84/01718 A1 | 5/1984 |
| WO | 86/07269 A1 | 12/1986 |
| WO | 95/13838 A1 | 5/1995 |
| WO | WO-9513838 A1 | 5/1995 |
| WO | 96/41159 A1 | 12/1996 |
| WO | 99/17749 A1 | 4/1999 |
| WO | WO-9917749 A1 | 4/1999 |
| WO | 99/38552 A1 | 8/1999 |
| WO | WO-9938552 A1 | 8/1999 |
| WO | 99/62576 A1 | 12/1999 |
| WO | WO-9962576 A1 | 12/1999 |
| WO | 00/26367 A2 | 5/2000 |
| WO | WO-0026367 A2 | 5/2000 |
| WO | 00/40089 A1 | 7/2000 |
| WO | WO-0040089 A1 | 7/2000 |
| WO | 00/72900 A1 | 12/2000 |
| WO | 00/74751 A1 | 12/2000 |
| WO | 01/12158 A1 | 2/2001 |
| WO | WO-0112158 A1 | 2/2001 |
| WO | 01/21234 A1 | 3/2001 |
| WO | WO-0121234 A1 | 3/2001 |
| WO | 01/26706 A2 | 4/2001 |
| WO | 01/56634 A1 | 8/2001 |
| WO | WO-0156634 A1 | 8/2001 |
| WO | 01/66173 A1 | 9/2001 |
| WO | WO-0166173 A1 | 9/2001 |
| WO | 01/94784 A1 | 12/2001 |
| WO | WO-0194784 A1 | 12/2001 |
| WO | 02/40083 A2 | 5/2002 |
| WO | 02/067688 A1 | 9/2002 |
| WO | 03/002170 A2 | 1/2003 |
| WO | WO-03002170 A2 | 1/2003 |
| WO | 03/009774 A2 | 2/2003 |
| WO | 03/009774 A2 | 3/2003 |
| WO | WO-03024360 A1 | 3/2003 |
| WO | 03/072193 A1 | 9/2003 |
| WO | 03/090509 A2 | 11/2003 |
| WO | 2004/002878 A2 | 1/2004 |
| WO | 2004/014969 A1 | 2/2004 |
| WO | WO-2004014969 A1 | 2/2004 |
| WO | 2004/026281 A2 | 4/2004 |
| WO | 2004/066871 A2 | 8/2004 |
| WO | 2004/067066 A1 | 8/2004 |
| WO | WO-2004066871 A2 | 8/2004 |
| WO | 2004/073551 A2 | 9/2004 |
| WO | WO-2004073551 A2 | 9/2004 |
| WO | 2005/034814 A1 | 4/2005 |
| WO | 2005/046769 A2 | 5/2005 |
| WO | WO-2005046769 A2 | 5/2005 |
| WO | 2006/012280 A1 | 2/2006 |
| WO | 2006/014793 A1 | 2/2006 |
| WO | WO-2006012280 A1 | 2/2006 |
| WO | WO-2006014793 A1 | 2/2006 |
| WO | 2006/026768 A1 | 3/2006 |
| WO | 2006/060586 A1 | 6/2006 |
| WO | 2006/075016 A1 | 7/2006 |
| WO | WO-2006075016 A1 | 7/2006 |
| WO | 2006/121921 A2 | 11/2006 |
| WO | 2007/035621 A1 | 3/2007 |
| WO | 2007/065944 A1 | 6/2007 |
| WO | 2007/084765 A2 | 7/2007 |
| WO | WO-2007084765 A2 | 7/2007 |
| WO | 2007/106557 A2 | 9/2007 |
| WO | WO-2007106557 A2 | 9/2007 |
| WO | 2007/112328 A2 | 10/2007 |
| WO | 2007/125456 A2 | 11/2007 |
| WO | 2007/138590 A2 | 12/2007 |
| WO | 2008/024808 A2 | 2/2008 |
| WO | 2008/054788 A2 | 5/2008 |
| WO | 2008/139460 A2 | 11/2008 |
| WO | 2008/151667 A1 | 12/2008 |
| WO | 2009/015389 A2 | 1/2009 |
| WO | 2009/048144 A1 | 4/2009 |
| WO | 2009/086112 A2 | 7/2009 |
| WO | WO-2009086112 A2 | 7/2009 |
| WO | 2009/137780 A2 | 11/2009 |
| WO | 2011/022484 A1 | 2/2011 |
| WO | 2011/025913 A1 | 3/2011 |
| WO | 2011/028997 A1 | 3/2011 |
| WO | 2011/133724 A2 | 10/2011 |
| WO | 2011/133724 A3 | 1/2012 |
| WO | 2013/075109 A2 | 5/2013 |
| WO | 2013/075109 A9 | 7/2013 |
| WO | 2013/075109 A3 | 10/2013 |
| WO | 2014/047638 A1 | 3/2014 |
| WO | 2014/047657 A2 | 3/2014 |
| WO | 2014/047657 A3 | 7/2014 |
| WO | 2015/048093 A2 | 4/2015 |

OTHER PUBLICATIONS

Examination Report in European Patent Application No. 07753177.0, mailed on Feb. 5, 2010, 3 pages.
Extended Search Report issued for European Patent Application No. 11153615.7, mailed on Dec. 15, 2011, 8 pages.
Examination Report in European Patent Application No. 11153618.1, mailed on Oct. 14, 2013, 5 pages.
Extended Search Report issued for European Patent Application No. 11153618.1, mailed on Dec. 12, 2011, 9 pages.
Extended Search Report issued for European Patent Application No. 13168508.3, mailed on Oct. 24, 2013, 7 pages.
Office Action mailed on Apr. 9, 2013 for Japanese Patent Application No. 2010-539873, English translation of "Notification of Reason for Rejection", 6 pages.
Examination Report in Mexican Patent Application No. MX/a/2008/011714, mailed on Jan. 19, 2012.
Examination Report in Mexican Patent Application No. MX/a/2010/012213, mailed on Jan. 16, 2014, 3 pages.
International Application Serial No. PCT/US2007/006530, International Search Report and Written Opinion mailed on Nov. 12, 2007, 15 pages.
International Application Serial No. PCT/US2007/006530, Invitation to Pay Additional Fees and Partial International Search mailed on Jul. 31, 2007, 7 pages.
International Application Serial No. PCT/US2008/087690, International Search Report and Written Opinion mailed on Aug. 11, 2009, 15 pages.
International Application Serial No. PCT/US2008/087690, Invitation to Pay Additional Fees and Partial International Search mailed on May 15, 2009, 5 pages.

(56) References Cited

OTHER PUBLICATIONS

International Application Serial No. PCT/US2009/030019, International Search Report and Written Opinion mailed on Jul. 20, 2009, 16 pages.
International Application Serial No. PCT/US2009/030019, Invitation to Pay Additional Fees and Partial International Search mailed on Jun. 5, 2009, 5 pages.
International Application Serial No. PCT/US2009/043313, International Search Report and Written Opinion mailed on Feb. 25, 2010, 16 pages.
International Application Serial No. PCT/US2009/043313, Invitation to Pay Additional Fees and Partial International Search mailed on Nov. 16, 2009, 6 pages.
International Application Serial No. PCT/US2009/043317, International Search Report and Written Opinion mailed on Feb. 16, 2010, 15 pages.
International Application Serial No. PCT/US2009/043317, Invitation to Pay Additional Fees and Partial International Search, mailed on Nov. 16, 2009, 5 pages.
International Application Serial No. PCT/US2009/043325, International Search Report and Written Opinion mailed on Nov. 12, 2009, 18 pages.
International Application Serial No. PCT/US2010/045897, International Search Report and Written Opinion mailed on Dec. 28, 2010, 12 pages.
International Application Serial No. PCT/US2010/047811, Invitation to Pay Additional Fees and Partial Search Report mailed on Dec. 2, 2010, 8 pages.
International Application Serial No. PCT/US2011/033329, International Search Report and Written Opinion mailed Nov. 23, 2011, 16 pages.
International Application Serial No. PCT/US2011/033329, Invitation to Pay Additional Fees and Partial Search Report, mailed Aug. 4, 2011, 5 pages.
International Application Serial No. PCT/US2011/044508, International Search Report and Written Opinion mailed Dec. 1, 2011, 11 pages.
International Application Serial No. PCT/US2013/061494, Invitation to Pay Additional Fees and Partial Search Report, mailed Jan. 28, 2014, 6 pages.
"Krupin Eye Valve with Scleral Buckle, Krupin Eye Valve With Disk", Hood Laboratories Catalogue, F 079 Rev., Nov. 1992, 4 pages.
"The Optimed Advantage—Glaucoma Pressure Regulator", Optimed Advertising Brochure, Journal of Glaucoma, vol. 2, No. 3, 1993, 4 pages.
Chen et al., "Floating-Disk Parylene Micro Check Valve", Micro Electro Mechanical Systems, MEMS, IEEE 20th International Conference, Jan. 21-25, 2007, pp. 453-456.
Chen et al., "Floating-Disk Parylene Microvalve for Self-Regulating Biomedical Flow Controls", Micro Electro Mechanical Systems, MEMS, IEEE 21st International Conference., Jan. 13-17, 2008, pp. 575-578.
Chen et al., "Surface-Micromachined Parylene Dual Valves for On-Chip Unpowered Microflow Regulation", Journal of Microelectromechanical Systems, vol. 16, No. 2, Apr. 2007, pp. 223-231.
Choudhri et al., "A Comparison of Dorzolamide-Timolol Combination Versus the Concomitant Drugs", American Journal of Ophthalmology, vol. 130, No. 6, Dec. 2000, pp. 832-833.
Durham, N.C., "FDA Approves an Industry First!—The MED-EL Cochlear Implant System is FDA Approved for Use With Magnetic Resonance Imaging (MRI)", PR Newswire, Jun. 18, 2003, 3 pages.
Eliason et al., "An Ocular Perfusion System", Investigate Ophthalmology Visual Science, vol. 19, No. 1, Jan. 1980, pp. 102-105.
Hashizoe et al., "Scleral Plug of Biodegradable Polymers for Controlled Drug Release in the Vitreous", Arch Ophthalmology, vol. 112, No. 10, Oct. 1994, pp. 1380-1384.
Jabs, Douglas A., "Treatment of Cytomegalovirus Retinitis—1992", Arch Ophthalmology, vol. 110, No. 2, Feb. 1992, pp. 185-187.

Khouri et al., "Use of Fixed-Dose Combination Drugs for the Treatment of Glaucoma", Drugs & Aging, vol. 24, No. 12, Dec. 2007, pp. 1007-1016.
Kimura et al., "A New Vitreal Drug Delivery System Using an Implantable Biodegradable Polymeric Device", Investigative Ophthalmology & Visual Science, vol. 35, No. 6, May 1994, pp. 2815-2819.
Lo et al., "A Refillable Polymer Drug Delivery Device for Treatment of Ocular Diseases", The Royal Society of Chemistry, Jan. 1, 2007, 28 pages.
Michelson et al., "Experimental EndophtalmitisTreated With an Implantable Osmotic Minipump", Arch. Ophthalmology, vol. 97, Jul. 1979, pp. 1345-1346.
Miki et al., "A Method for Chronic Drug Infusion Into the Eye", Japanese Journal of Ophthalmology, vol. 28, No. 2, 1984, pp. 140-146.
Pincus et al., "Why are Only 50% of Courses of Anti-Tumor Necrosis Factor Agents Continued for Only 2 Years in Some Settings? Need for Longterm Observations in Standard Care to Compliment Clinical Trials", Journal of Reumatology, vol. 33, No. 12, Dec. 2006, pp. 2372-2375.
Pope et al., "MRI in Patients with High-Grade Gliomas Treated with Bevacizumab and Chemotherapy", Neurology, vol. 66, No. 8, Apr. 2006, pp. 1258-1260.
Rubsamen et al., "Prevention of Experimental Proliferative Vitreoretinopathy With a Biodegradable Intravitreal Implant for the Sustained Release of Fluorouracil", Arch. Ophthalmology, vol. 112, No. 3, Mar. 1994, pp. 407-413.
Sanborn et al., "Sustained-Release Ganciclovir Therapy for Treatment of Cytomegalovirus Retinitis", Arch Ophthmology, vol. 110, No. 2, Feb. 1992, pp. 188-195.
Smith et al., "Intravitreal Sustained-Release Ganciclovir", Arch Ophthlmology, vol. 110, No. 2, Feb. 1992, pp. 255-258.
Stark-Vance, "Bevacizumab and CPT-11 in the Treatment of Relapsed Malignant Glioma", Neuro Oncology, vol. 7, No. 3, Abstract from the World Federation of Neuro-Oncology Second Quadrennial Meeting and Sixth Meeting of the European Association for Neuro-Oncology, May 5-8, 2005, Abstract 342, Jul. 2005, p. 369.
Steyer, Robert, "Alcon Eye-Drug Setback Raises the Stakes", Available online at <http://www.thestreet.com/story/10187873/1/alcon-eye-drug-setback-raises-the-stakes.html>, Oct. 14, 2004, 4 pages.
Strohmaier et al., "The Efficacy and Safety of the Dorzolamide-Timolol Combination Versus the Concomitant Administration of its Components", Ophthalmology, vol. 105, No. 10, Oct. 1998, pp. 1936-1944.
Xie et al., "An Electrochemical Pumping System for On-Chip Gradient Generation", Analytical Chemistry, vol. 76, No. 13, May 2004, pp. 3756-3763.
Examination Report Received for Chinese Patent Application No. 201080046911.8 mailed on Dec. 3, 2014, 6 pages (in accordance with 37 CFR § 1.98(a) (3)).
Examination Report Received for Mexican Patent Application No. MX/a/2012/002063 mailed on Feb. 27, 2015.
Examination Report Received for Mexican Patent Application No. MX/a/2010/012213 mailed on Jan. 5, 2015.
PCT International Patent Application No. PCT/US2011/033329, International Preliminary Report on Patentability mailed Nov. 1, 2012, 13 pages.
PCT International Patent Application No. PCT/US2010/045897, International Preliminary Report on Patentability mailed Mar. 1, 2012, 9 pages.
Examination Report Received for European Patent Application No. 10760475.3, mailed on Apr. 7, 2015, 7 pages.
PCT International Patent Application No. PCT/US2013/061443, International Preliminary Report on Patentability issued Mar. 24, 2015, 9 pages.
PCT International Patent Application No. PCT/US2013/061494, International Preliminary Report on Patentability issued Mar. 24, 2015, 13 pages.
PCT International Patent Application No. PCT/US2014/057158, International Search Report and Written Opinion mailed Mar. 30, 2015, 14 pages.

(56) References Cited

OTHER PUBLICATIONS

First Examiner Report received for Australian Application No. 2010284216 mailed Mar. 20, 2014, 5 pages.
Examiner Report received for Japanese Application No. 2011-508709 mailed Mar. 4, 2014, 5 pages (3 pages of English Translation and 2 pages of Office Action).
Examination Report received for Chinese Patent Application No. 201180030341.8 mailed Jul. 2, 2014, 7 pages.
Examination Report received for Chinese Patent Application No. 200980126549.2 mailed Apr. 28, 2014, 3 pages.
Examination Report received for Chinese Patent Application No. 201080046911.8 mailed May 6, 2014, 8 pages.
Examination Report received for Japanese Patent Application No. 2012-525667 mailed on Jun. 6, 2014, 9 pages (5 pages of English Translation and 4 pages.
Examination Report received for Mexican Patent Application No. MX/a/2010/012213 mailed Apr. 16, 2014.
Examination Report received for Mexican Patent Application No. MX/a/2013/013831 mailed on Mar. 26, 2014, 1 page.
International Application No. PCT/US2012/065874, International Preliminary Report on Patentability mailed May 30, 2014, 7 pages.
International Application No. PCT/US2012/065874, International Search Report and Written Opinion mailed Aug. 7, 2013, 13 pages.
International Application No. PCT/US2013/061443, International Search Report mailed on Jan. 21, 2014, 3 pages.
International Application No. PCT/US2013/061494, international Search Report and Written Opinion mailed May 28, 2014, 21 pages.
Sanborn GE et al. "Sustained-release ganciclovir therapy for treatment of cytomegalovirus retinitis. Use of an intravitreal device." Archives of Ophthalmology, vol. 110(2): Feb. 1992, pp. 188-195.
Invitation to pay Additional Fees and Partial International Search for PCT Application No. PCT/US2009/043317, mailed Nov. 16, 2009, 5 pages.
Invitation to Pay Additional Fees and Partial International Search for PCT Application No. PCT/US2009/043313, mailed Nov. 16, 2009, 6 pages.
International Search Report for PCT Application No. PCT/US2009/043325, mailed Dec. 11, 2009, 9 pages.
Written Opinion for PCT Application No. PCT/US2009/043325, mailed Dec. 11, 2009, 9 pages.
Examination Report for European Patent Application No. 07753177.0, mailed Feb. 5, 2010, 3 pages.
International Search Report for PCT Application No. PCT/US2009/043317, mailed Feb. 16, 2010, 7 pages.
Written Opinion for PCT Application No. PCT/US2009/043317, mailed Feb. 16, 2010, 8 pages.
International Search Report for PCT Application No. PCT/US2009/043313, mailed Feb. 25, 2010, 8 pages.
Written Opinion for PCT Application No. PCT/US2009/043313, mailed Feb. 25, 2010, 8 pages.
"FDA Approves and Industry First!—The MED-EL Cochlear Implant System in FDA Approved for Use With Magnetic Resonance Imaging (MRI)," PR Newwire, Durham, N.C., Jun. 18, 2003, 3 pages.
"Krupin Eye Valve with Scleral Buckle, Krupin Eye Valve With Disk," Hood Laboratories Catalogue, F 079 Rev. Nov. 1992, 4 pages.
"The Optimed Advantage—Glaucoma Pressure Regulator," Optimed Advertising Brochure, Journal of Glaucoma, vol. 2, No. 3, 1993, 4 pages.
Chen et al. "Floating-Disk Parylene Micro Check Valve," Micro Electro Mechanical Systems, 2007, IEEE 20th International Conference on MEMS, Jan. 21-25, 2007, 4 pages.
Chen et al. "Floating-Disk Parylene Microvalve for Self-Regulating Biomedical Flow Controls," IEEE 21st International Conference on MEMS, 2008, Jan. 13-17, 2008, 4 pages.
Chen et al. "Surface-Micromachined Parylene Dual Valves for On-Chip Unpowered Microflow Regulation," Journal of Microelectromechanical Systems, vol. 16, No. 2, Apr. 2007, pp. 223-231.
Choudhri et al. "A Comparison of Dorzolamide-Timolol Combination Versus the Concomiltant Drugs," American Journal of Ophthalmology, Dec. 2000, 130, pp. 832-833.
Eliason et al. "An Ocular Perfusion System," Invent. Opthalmol. Vis. Sci., vol. 19, No. 1, Jan. 1980, pp. 102-105.

Hashizoe et al. "Scleral Plug of Biodegradable Polymers for Controlled Release in the Vitreous" Arch Ophthalmol, vol. 112, Oct. 1994, pp. 1380-1384.
Jabs "Treatment of Cytomegalovirus Retinitis—1992," Arch Ophthlmol, vol. 110, Feb. 1992, pp. 185-187.
Khouri et al. "Use of Fixed-Dose Combination Drugs for the Treatment of Glaucoma," Drugs Aging, 2007, 24, 12, pp. 1007-1016.
Kimura et al. "A New Vitreal Drug Delivery System Using an Implantable Biodegradable Polymeric Device," Investigative Ophthalmology & Visual Science, May 1994, vol. 35, No. 6; pp. 2815-2819.
Lo et al. "A Refillable Polymer Drug Delivery Device for Treatment of Ocular Diseases," The Royal Society of Chemistry, Jan. 1, 2007, 28 pages.
Michelson et al. "Experimental Endophtalmitis Treated With an Implantable Osmotic Minipump," Arch Opthalmol, vol. 97, Jul. 1979, pp. 1345-1346.
Miki, et al. "A Method for Chronic Drug Infusion Into the Eye," Japanese Journal of Ophthalmology, vol. 28, 1984, pp. 140-146.
Pincus et al. "Why are Only 50% of Courses of Anti-Tumor Necrosis Factor Agents Continued for Only 2 Years in Some Settings? Need for Longterm Observations in Standard Care to Compliment Clinical Trials," Journal of Rheumatology, 2006, 33, 12, pp. 2372-2375.
Pope et al. "MRI in Patients with High-Grade Gliomas Treated with Bevacizumab and Chemotherapy," Neurology, 2006, 66, pp. 1258-1260.
Rubsamen et al. "Prevention of Experimental Proliferative Viteoretinopathy With a Biodegradable Intravitreal Implant for the Sustained Release of Fluorouracil," Arch Ophthalmol, vol. 112, Mar. 1994, pp. 407-413.
Sanborn et al. "Sustained-Release Ganciclovir Therapy for Treatment of Cytomegalovirus Retinitis," Arch Ophthmol, vol. 110, Feb. 1992; pp. 188-195.
Smith et al. "Intravitreal Sustained-Release Ganiclovir," Arch Ophthlmol, vol. 110, Feb. 1992, pp. 255-258.
Stark-Vance, "Bevacizumab and CPT-11 in the Treatment of Relapsed Malignant Glioma," Abstract form the World Federation of Neuro-Oncology Second Quadrennial meeting and Sixth meeting of the European Association for neuro-Oncology, May 5-8, 2005, Abstract 342, p. 369.
Steyer "Alcon Eye-Drug Setback Raises the Stakes," The Street. Com, Oct. 14, 2004, 4 pages.
Strohmaier et al. "The Efficacy and Safety of the Dorzlamide-Timolol Combination Versus the Concomitant Administration of its Components," Ophthalmology, Oct. 1998, vol. 105, No. 10, pp. 1936-1944.
Xie et al. "An Electrochemical Pumping System for On-Chip Gradient Generation," Analytical Chemistry, Jul. 1, 2004, 8 pages. (A-H).
Examination Report for European Patent Application No. 07753177.0, mailed Jan. 29, 2009, 6 pages.
Invitation to Pay Additional Fees and Partial International Search for PCT Application No. PCT/US2007/006530, mailed Jul. 31, 2007, 7 pages.
International Search Report for PCT Application No. PCT/US2007/006530, mailed Nov. 12, 2007, 7 pages.
Written Opinion for PCT Application No. PCT/US2007/006530, mailed Nov. 12, 2007, 10 pages.
Invitation to Pay Additional Fees and Partial International Search for PCT Application No. PCT/US2009/030019, mailed Jun. 5, 2009, 5 pages.
International Search Report for PCT Application No. PCT/US2009/030019, mailed Jul. 20, 2009, 7 pages.
Written Opinion for PCT Application No. PCT/US2009/030019, mailed Jul. 20, 2009, 9 pages.
Invitation to Pay Additional Fees and Partial International Search for PCT Application No. PCT/US2008/087690, mailed May 15, 2009, 5 pages.
International Search Report for PCT Application No. PCT/US2008/087690, mailed Aug. 11, 2009, 7 pages.
Written Opinion for PCT Application No. PCT/US2008/087690, mailed Aug. 11, 2009, 10 pages.
Examination Report Received for Mexican Patent App. No. MX/A/2012/012133 mailed on Sep. 25, 2014.

* cited by examiner

DRUG-DELIVERY PUMP WITH DYNAMIC, ADAPTIVE CONTROL

CROSS-REFERENCE TO RELATED APPLICATIONS

This application is a divisional application of, and incorporate herein by reference, U.S. patent application Ser. No. 12/858,808, filed on Aug. 18, 2010 continuation-in-part of, claims priority to and the benefit of, and incorporates herein by reference in its entirety U.S. patent application Ser. No. 12/463,265, which was filed on May 8, 2009, and which claimed priority to and the benefit of U.S. Provisional Patent Application Nos. 61/051,422, filed on May 8, 2008; 61/197,751, filed on Oct. 30, 2008; 61/197,769, filed on Oct. 30, 2008; 61/198,090, filed on Nov. 3, 2008; and 61/198,131, filed on Nov. 3, 2008. This application also claims priority to and the benefit of, and incorporates herein by reference in its entirety, U.S. Provisional Patent Application No. 61/234,742, which was filed on Aug. 18, 2009.

TECHNICAL FIELD

In various embodiments, the invention relates to drug-delivery pumps. In particular, embodiments of the invention relate to drug-delivery pumps whose actuation may be dynamically and adaptively controlled.

BACKGROUND

Medical treatment often requires the administration of a therapeutic agent (e.g., medicament, drugs, etc.) to a particular part of a patient's body. As patients live longer and are diagnosed with chronic and/or debilitating ailments, the likely result will be an increased need to place even more protein therapeutics, small-molecule drugs, and other medications into targeted areas throughout the patient's body. Some maladies, however, are difficult to treat with currently available therapies and/or require administration of drugs to anatomical regions to which access is difficult to achieve.

A patient's eye is a prime example of a difficult-to-reach anatomical region, and many vision-threatening diseases, including retinitis pigmentosa, age-related macular degeneration (AMD), diabetic retinopathy, and glaucoma, are difficult to treat with many of the currently available therapies. For example, oral medications can have systemic side effects; topical applications may sting and engender poor patient compliance; injections generally require a medical visit, can be painful, and risk infection; and sustained-release implants must typically be removed after their supply is exhausted (and generally offer limited ability to change the dose in response to the clinical picture).

Another example is cancer, such as breast cancer or meningiomas, where large doses of highly toxic chemotherapies, such as rapamycin, bevacizumab (e.g., AVASTIN), or irinotecan (CPT-11), are typically administered to the patient intravenously, which may result in numerous undesired side effects outside the targeted area. Yet another example is drug delivery to the knee, where drugs often have difficulty penetrating the avascular cartilage tissue for diseases such as osteoarthritis.

Implantable drug-delivery devices (e.g., drug-delivery pumps), which may have a refillable drug reservoir, a cannula for delivering the drug, a check valve, etc., generally allow for controlled delivery of pharmaceutical solutions to a specified target. As drug within the drug reservoir depletes, the physician can refill the reservoir with, for example, a syringe, while leaving the device implanted within the patient's body. This approach can minimize the surgical incision needed for implantation and typically avoids future or repeated invasive surgery or procedures.

Implantable drug-delivery pumps, particularly in ocular applications, often utilize a passive mechanism for drug delivery (e.g., pumping the drug out when a finger is pressed on the drug reservoir). One limitation of these conventional, passively-driven drug-delivery pumps is their inability to dynamically respond to changes inside the pump (e.g., failures, blockages, etc.) or to changes in the drug-delivery target area (e.g., increased pressure, bending of the pump's cannula, inflammation causing pressure around the cannula, etc.). The ability to respond to such changes can improve not only the therapeutic value of a pump, but also safety.

Active drug-delivery pumps, particularly feedback-driven ones, represent a substantial improvement over passively-driven pumps. Typically, these feedback-driven pumps are electrically-driven mechanical pumps. They generally employ controller units that receive inputs from sensors that monitor the target treatment area and, in response, direct the release of a pharmaceutical or therapeutic agent to achieve a desired result. The amount of drug released in each dosage period is thus largely determined by the current conditions of the target area and is intended to be variable depending on what the conditions of the target area warrant.

Pharmaceutical treatment regimens may, however, require that a drug be administered in fixed amounts at regular time intervals regardless of the changing conditions in the drug-delivery target area. Since the dosage levels produced by existing closed-loop feedback-driven systems can be highly dependent on the parameters of the treatment area and thus prone to fluctuations, they are inadequate for delivering fixed drug dosages at periodic intervals. For example, changes in the conditions of the target area, such as blockages or other biochemical or physiological events, may lead to variable levels of drug being delivered to the target area. Accordingly, there is a need for a feedback-driven pump that maintains the target dosage level despite such changes.

Furthermore, while feedback based on the conditions of the target area is important in numerous therapeutic applications, errors in drug administration can also arise from changing conditions within the pump itself. Conventional pumps generally do not account for such changes, which can also lead to variable amounts of drug being released. Accordingly, there is also a need for a drug-delivery pump that dynamically responds to changing conditions within the pump itself in order to, for example, consistently release a fixed dosage of drug at periodic time intervals.

SUMMARY OF THE INVENTION

In various embodiments, the present invention features an external or implantable drug-delivery pump that includes a dynamic, adaptive control system. The control system may operate the pump so as to release substantially fixed amounts of pharmaceutical or therapeutic agents to a target treatment area at regular intervals. In certain embodiments, the control system continuously monitors (either directly or indirectly) conditions internal to the pump that have an effect on the degree and duration of pump actuation and, consequently, the amount of drug that is released. As used herein, the term "substantially" means ±10% (e.g., by weight or by volume), and in some embodiments, ±5%.

In one embodiment, the drug-delivery pump is an electro-chemically-actuated pump, such as an electrolysis-driven pump. Electrochemically-actuated pumps, as compared to electrically-driven mechanical pumps, offer several advantages for drug-delivery systems. For example, they generally have few moving parts, which enables them to be small and portable, and which makes them less prone to mechanical breakdown than electrically-driven mechanical pumps. In particular, electrochemically-actuated pumps are suitable for environments that require small pump sizes, such as the ocular environment. As further described herein, an electrolysis-driven pump generally employs electrodes to generate an electrochemically active gas that variably pressurizes a drug contained in a separate chamber in order to dispense the drug in a controlled fashion. The amount of drug dispensed depends on the gas pressure variably generated by the pump actuator, which in turn depends on the current that passes through the electrodes. Because of the inherent variability in these electrolysis-driven pumps (e.g., the volume of gas and/or the amount of electrolyte can change between every pump cycle), the adaptive control design described herein can confer substantial advantages, as further explained below.

In general, in one aspect, embodiments of the invention feature a drug-delivery pump that includes a drug reservoir, a cannula for conducting liquid from the reservoir to a target site, a pump actuator for forcing the liquid from the reservoir through the cannula, and circuitry for controlling the actuator based on a change in a condition of the pump.

In general, in another aspect, embodiments of the invention feature a method of delivering a drug to a patient using such a drug-delivery pump. The method involves establishing fluid communication between the drug reservoir and the patient (i.e., the target site) and controlling the pump actuator based on a change in a condition of the pump so as to deliver a dosage of liquid from the drug reservoir into the patient.

In various embodiments, the control circuitry maintains delivery of a substantially fixed dosage of the liquid at periodic time intervals to the target site. Moreover, the circuitry may include memory for storing the conditions of the pump at the time of previous delivery events (e.g., at the time of each delivery interval). In one embodiment, the drug-delivery pump includes a flow sensor for measuring a flow rate of the liquid through the cannula and into the patient, and the circuitry controls the pump actuator based, at least in part, on an analysis of the flow rate. The circuitry may also control the actuator based on the stored conditions of the pump from the previous doses and/or on real-time data from the actuator. In another embodiment, the control circuitry maintains delivery of a substantially fixed dosage of the liquid over time through continuous infusion to the target site.

As mentioned, the drug-delivery pump may be an electrolysis-driven pump. More particularly, the pump actuator may include an electrolyte chamber, an expandable diaphragm that separates the electrolyte chamber from the drug reservoir and provides a fluid barrier therebetween, and electrolysis electrodes that cause evolution of a gas in the electrolyte chamber. The evolution of the gas expands the diaphragm so that the liquid is forced from the drug reservoir into the cannula. In various embodiments, the diaphragm expansion is adjusted by varying the actuation current supplied to the electrodes. In other embodiments, the diaphragm expansion is adjusted by varying an actuation duration of the electrodes. As described herein, the electrolysis electrodes may be driven with either a constant current or a time-varying current waveform.

In general, in yet another aspect, embodiments of the invention feature a drug-delivery pump that includes a drug reservoir, an electrolyte chamber, electrolysis electrodes, an expandable diaphragm that separates the electrolyte chamber from the drug reservoir and provides a fluid barrier therebetween, a cannula for conducting liquid from the drug reservoir to a target site, and circuitry for adjusting expansion of the diaphragm based on conditions of the target site (e.g., changes in one or more biochemical parameters of the target site, in electrical activity at the target site, and/or in pressure at the target site). The pump may include a sensor for detecting such conditions. For their part, the electrolysis electrodes may be activated to cause evolution of a gas in the electrolyte chamber, which expands the diaphragm so that the liquid is forced from the drug reservoir into the cannula.

In general, in still another aspect, embodiments of the invention feature a drug-delivery pump that includes a drug reservoir, a cannula for conducting liquid from the reservoir to a target site, a pump actuator for forcing the liquid from the reservoir through the cannula, and circuitry for controlling the actuator. In particular, the circuitry controls the actuator i) to initially deliver a substantially fixed dosage of the liquid at periodic time intervals to the target site, and ii) to compensate for a change in a condition of the pump so as to maintain or resume the delivery of the substantially fixed dosage of the liquid at the periodic time intervals to the target site.

In general, in a further aspect, embodiments of the invention feature a method of delivering a drug to a patient from a drug-delivery pump that includes a drug reservoir and a pump actuator for forcing liquid from the reservoir into the patient. The method involves establishing fluid communication between the drug reservoir and the patient, and controlling the pump actuator. In particular, the actuator is controlled i) to initially deliver a substantially fixed dosage of the liquid at periodic time intervals from the drug reservoir into the patient, and ii) to compensate for a change in a condition of the pump so as to maintain or resume the delivery of the substantially fixed dosage of the liquid at the periodic time intervals into the patient.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations, even if not made explicit herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DESCRIPTION

In general, embodiments of the present invention pertain to external or implantable drug-delivery pumps (whether they be reusable and refillable pumps, disposable pumps, etc.) whose actuation may be dynamically and adaptively controlled. For example, embodiments of the drug-delivery pumps may be implantable within a patient's body, such as within the patient's eye or brain. In certain embodiments, the implantable drug-delivery pumps combine small size and a refillable drug reservoir. The small size minimizes discomfort from the drug-delivery pump to the patient, while the refillable reservoir allows the pump to be refilled in situ, rather than having to be replaced. As such, a fluid, such as a solution of a drug, can be supplied to the patient over extended periods of time.

A. Exemplary Drug-Delivery Pump

Figure 1:
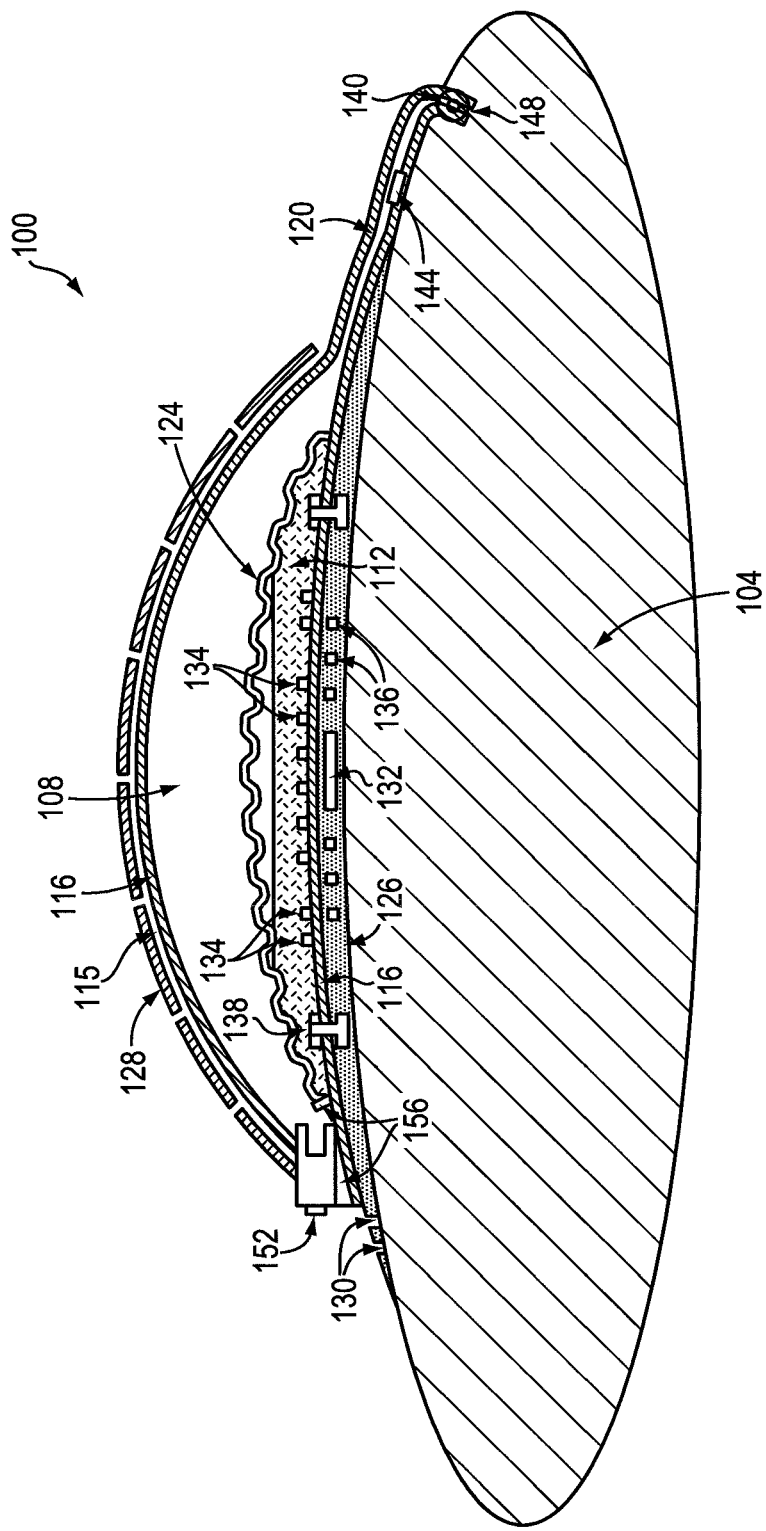
FIG. 1 schematically illustrates, in cross-section, an implantable drug-delivery pump in accordance with one embodiment of the invention.
Figure 2:
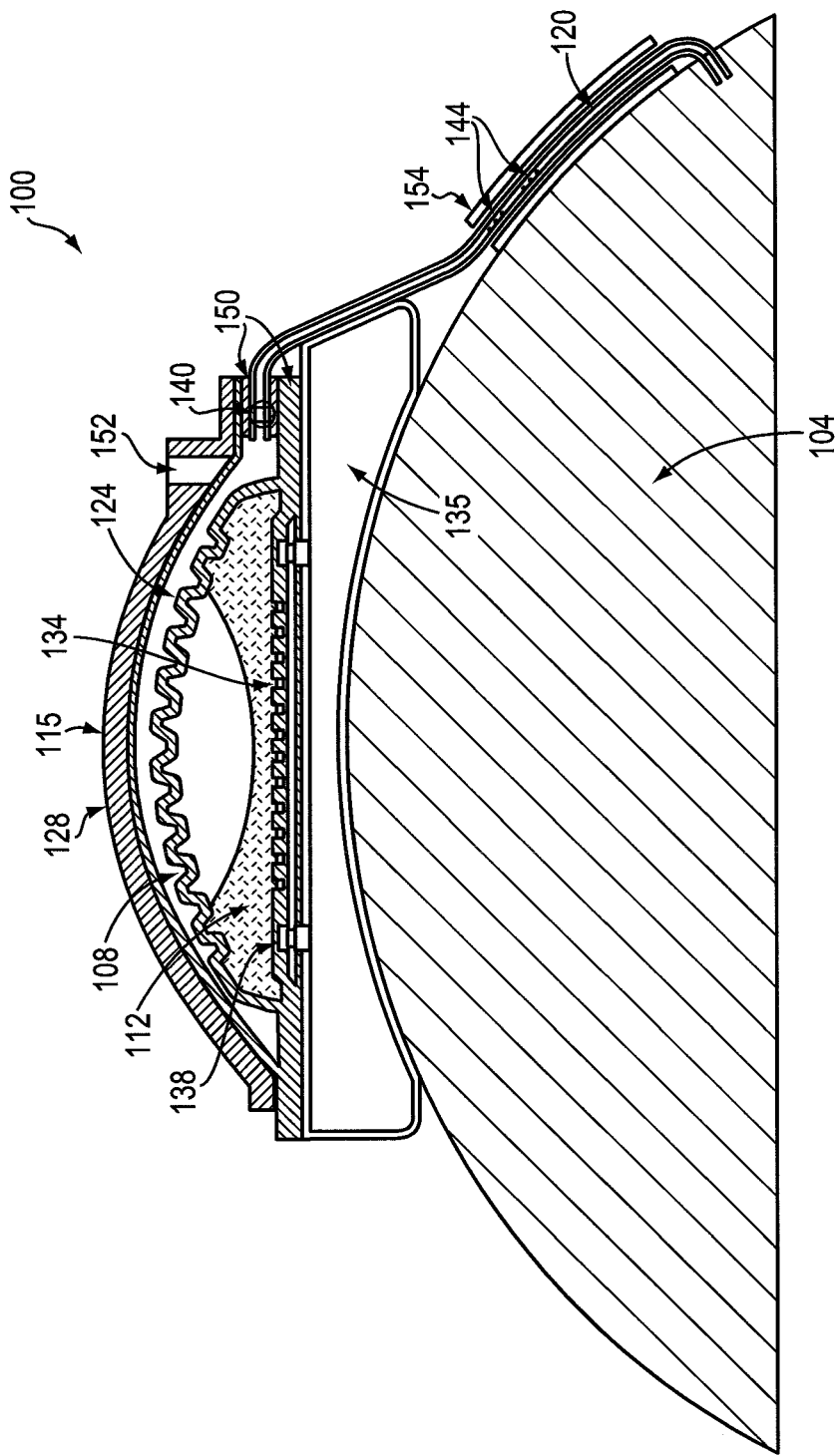
FIG. 2 schematically illustrates, in cross-section, an implantable drug-delivery pump in accordance with another embodiment of the invention.

Embodiments of the invention may be employed in connection with various types of drug-delivery pumps, whether they be external pumps or pumps implantable within a patient's body. FIGS. 1 and 2 schematically illustrate two variations of an exemplary implantable drug-delivery pump 100 (namely, an exemplary electrolytic or electrolysis-driven pump 100) implanted within a patient's eye 104. The pump 100 may, however, instead be implanted in other portions of a patient's body. For example, it may be implanted in the subarachnoid space of the brain to provide chemotherapy or to provide another type of treatment for the brain (e.g., by dosing the brain's parenchyma directly); near a tumor in any portion of the patient's body to provide chemotherapy; in a pancreas that does not respond well to glucose to provide agents (e.g., proteins, viral vectors, etc.) that will trigger insulin release; external to a patient but with a cannula placed under the skin or inside the abdominal cavity to deliver insulin; in the knee to provide drugs that will treat osteoarthritis or other cartilage diseases; near the spine to provide pain medications or anti-inflammatories; or elsewhere.

As illustrated in FIGS. 1 and 2, embodiments of the pump 100 may include two main components: a pair of chambers 108, 112 surrounded, at least in part, by a wall 115, and a cannula 120. As illustrated in FIG. 1, the wall 115 that surrounds the chambers 108, 112 may include or consist of a stand-alone parylene film 116 and, thereover, a separate protection shell 128 made of a relatively rigid biocompatible material (e.g., medical-grade polypropylene). Alternatively, as illustrated in FIG. 2, the wall 115 may correspond only to the protective shell 128, which may be coated with parylene.

The top chamber 108 defines a drug reservoir that, when being used to treat a patient, may contain the drug to be administered in liquid form. For its part, the bottom chamber 112 may contain a liquid that, when subjected to electrolysis, evolves a gaseous product. For example, that liquid may be water, which may be electrolytically separated by an applied voltage into hydrogen gas and oxygen gas. Alternatively, as other examples, the electrolyte liquid may be a saline solution (i.e., NaCl in $H_2O$) or a solution that contains either magnesium sulfate or sodium sulfate. In one embodiment, the two chambers 108, 112 are separated by a corrugated diaphragm 124. In other words, the diaphragm 124 provides a fluid barrier between the two chambers 108, 112. Like the stand-alone film 116, the diaphragm 124 may be constructed from, for example, parylene.

As illustrated in FIG. 1, the stand-alone film 116 may act as an outer barrier for the drug reservoir 108 and the protective shell 128 may provide a hard surface against which the film 116 exerts pressure. In such a case, the shell 128 may be perforated to allow for eye, brain, or other bodily fluid movement. Alternatively, as illustrated in FIG. 2, the protective shell 128 may itself act as the outer barrier for the drug reservoir 108 and be unperforated. In both embodiments depicted in FIGS. 1 and 2, the protective shell 128 may prevent outside pressure from being exerted on the drug reservoir 108. As illustrated in FIG. 1, a bottom portion 126 (i.e., a floor 126) of the protective shell 128 may include suture holes 130. Similarly, although not shown in either FIG. 1 or FIG. 2, the cannula 120 may also include suture holes along its sides. The suture holes 130 may be employed in suturing (i.e., anchoring) the pump 100 in place in the patient's body.

As also illustrated in FIG. 1, to provide power to the pump 100 and to enable data transmission therewith, a battery and control circuitry 132 may be embedded (e.g., hermetically sealed) under the chambers 108, 112 (i.e., between a bottom portion of the stand-alone parylene film 116 of the drug reservoir 108 and the floor 126 of the protective shell 128), and an induction coil 136 may be integrated in the protective shell 128 (e.g., by injection molding). FIG. 2 more clearly illustrates a hermetic case 135 for housing the battery and conventional control circuitry 132, but, for simplicity, does not depict the components housed therein. The hermetic case 135 may be made from biocompatible metals (e.g., titanium) or metal alloys. The bottom of the hermetic case 135 may be flat, or it may be concave to help the implantable pump 100 fit on the patient's eye 104.

In one embodiment, the induction coil 136 permits wireless (e.g., radio-frequency) communication with an external device (e.g., a handset). The handset may be used to send wireless signals to the control circuitry 132 in order to program, reprogram, operate, calibrate, or otherwise configure the pump 100. In one embodiment, the control circuitry 132 communicates electrically with electrolysis electrodes 134 in the electrolyte chamber 112 by means of metal interconnects (vias) 138 spanning a bottom portion of the electrolyte reservoir 112. The electrolysis electrodes 134 may be made from, for example, platinum, gold, and/or other metal(s). As further described below, the control circuitry 132 controls the pumping action of the pump 100, including the below-described closed-loop control process.

In one embodiment, as illustrated in FIG. 1, the cannula 120 connects the drug reservoir 108 to a check valve 140 inserted at the site of administration. The check valve 140 may be a one-way check valve that prevents the backflow of any fluid into the drug reservoir 108. Alternatively, or in addition, as illustrated in FIG. 2, the check valve 140 may be integral with and located at a proximal end of the cannula 120 (i.e., at the end closest to the drug reservoir 108). More generally, however, the check valve 140 may be located anywhere along the cannula 120. In addition, one or more flow sensors 144 for monitoring the flow of the drug, and thereby enabling the measurement of the drug volume delivered and/or the flow rate of the drug through the cannula 120, may be associated with one or more of a proximal, middle, or distal portion of the cannula 120. Optionally, as illustrated in FIG. 1, one or more target site sensor(s) 148 may also be integrated at a distal end of the cannula 120 (i.e., at the end furthest from the drug reservoir 108) in order to measure one or more parameters at the site of administration (e.g., the intravitreal chamber, shoulder capsule, knee capsule, cerebral ventricals, spinal canal, etc.). For example, the target site sensor(s) 148 may be employed to sense one or more of a change in a biological or biochemical parameter at the target site (e.g., a change in a specific analyte concentration, the presence or absence of a specific biochemical marker, etc.), a change in electrical activity at the target site (which may, for example, be brought on by a physiological change), and a change in pressure at the target site. In one embodiment, the target site sensor(s) 148 provide feedback (i.e., real-time measurements) to the control circuitry 132 so that the flow of drug may be metered by a closed-loop control process. For example, increased pressure in the drug target region may warrant a decrease in the flow of drug from the pump 100.

As illustrated in FIG. 1, the cannula 120 may be an extension of the stand-alone parylene film 116. Alternatively, as illustrated in FIG. 2, the cannula 120 may be a separate component (e.g., a parylene component) that is coupled to the protective shell 128. For example, a proximal end of the cannula 120 may be inserted through a fluid connection port formed in the protective shell 128 and bonded thereto by way of, e.g., a biocompatible epoxy glue 150. A silicone sheath 154 may be placed around a portion of the cannula 120 (see FIG. 2), but this is optional (see FIG. 1).

In one embodiment, as illustrated in FIG. 1, a fill port 152 is assembled with the drug reservoir 108 and sealed by a sealant (e.g., a biocompatible epoxy) 156 to the stand-alone film 116 and protective shell 128. In yet another embodiment, as illustrated in FIG. 2, a hole may be formed through the protective shell 128 and the fill port 152 featured therein. In still another embodiment, the fill port 152 may be formed elsewhere on the pump 100 and be connected to the drug reservoir 108 through tubing. For example, the fill port 152 may be molded from biocompatible materials, coupled to a matching notch on the hermetic case 135, and connected to the drug reservoir 108 through the tubing. In one embodiment, the tubing is inserted through a fluid connection port formed in a wall surrounding the drug reservoir 108 and bonded thereto by way of a biocompatible epoxy glue. In either case, the fill port 152 is in fluid communication with the drug reservoir 108 and permits an operator of the pump 100 (e.g., a physician) to refill the drug reservoir 108 in situ (e.g., while the pump 100 is implanted within the patient's eye 104). In general, the drug reservoir 108 can be refilled by inserting a refill needle into and through the fill port 152.

In various embodiments, the main parts of the pump 100 (i.e., the pair of chambers 108, 112 and the cannula 120) are amenable to monolithic microfabrication and integration using multiple parylene layer processes. The fill port 152, the protective shell 128, and other components may be assembled with the pump 100 after the microfabrication steps.

In operation, when current is supplied to the electrolysis electrodes 134, the electrolyte evolves gas, expanding the corrugated diaphragm 124 (i.e., moving the diaphragm 124 upwards in FIGS. 1 and 2) and forcing liquid (e.g., drug) out of the drug reservoir 108, into and through the cannula 120, and out the distal end thereof to the targeted site of administration. The corrugations or other folds in the expandable diaphragm 124 permit a large degree of expansion, without sacrificing volume within the drug reservoir 108 when the diaphragm 124 is relaxed. When the current is stopped, the electrolyte gas condenses back into its liquid state, and the diaphragm 124 recovers its space-efficient corrugations.

B. Adaptive Control Based Upon Internal Pump Conditions

In general, the response of the electrolysis-driven pump 100 to a given input current supplied to the electrolysis electrodes 134 depends on how much liquid is remaining in the drug reservoir 108. For example, if the drug reservoir 108 is nearly empty, more current is needed to bring the drug reservoir 108 to its "full" configuration before pressure can begin to build up and pumping can commence. On the other hand, if the drug reservoir 108 is completely full, very little current is needed before delivery of the drug begins. Similarly, the response of the electrolysis-driven pump 100 to a given input current also depends on the gas/liquid ratio in the electrolysis chamber 112. In particular, the response of the pump 100 will be very different when the drug reservoir 108 is full with drug (e.g., when the electrolysis chamber 112 operates with a low gas/liquid ratio) than when the drug reservoir 108 is nearly empty (e.g., when the electrolysis chamber 112 operates with a high gas/liquid ratio). In addition, other factors can cause the response of the electrolysis-driven pump 100 to change over time including, for example, degradation of the electrolysis electrodes 134, changes in the concentration of the electrolyte in the electrolysis chamber 112, changes in the flow characteristics of the check valve 140, and restrictions that form at the output of the cannula 120 due to tissue growth or some other mechanism.

Because of these factors, the electrolysis pump 100 is inherently variable. Accordingly, adaptive control in accordance herewith can confer substantial advantages upon the pump 100. For example, as further explained below, by analyzing previous doses to ascertain how the pump 100 responded to given input currents, the optimal settings (e.g., the settings which give the most accurate and shortest dose) for the current dose can be derived. This can be particularly beneficial when the dose volume is small compared to the volume of the drug reservoir 108. In such a situation, the state parameters of the pump 100 (e.g., the drug volume remaining in the drug reservoir 108, the liquid/gas ratio in the electrolysis chamber 112, the condition of the electrodes 134, the characteristics of the check valve 140, etc.) are nearly identical from one dose to the immediately following dose, and, as such, the previous doses are an excellent predictor for the current dose.

Figure 3:
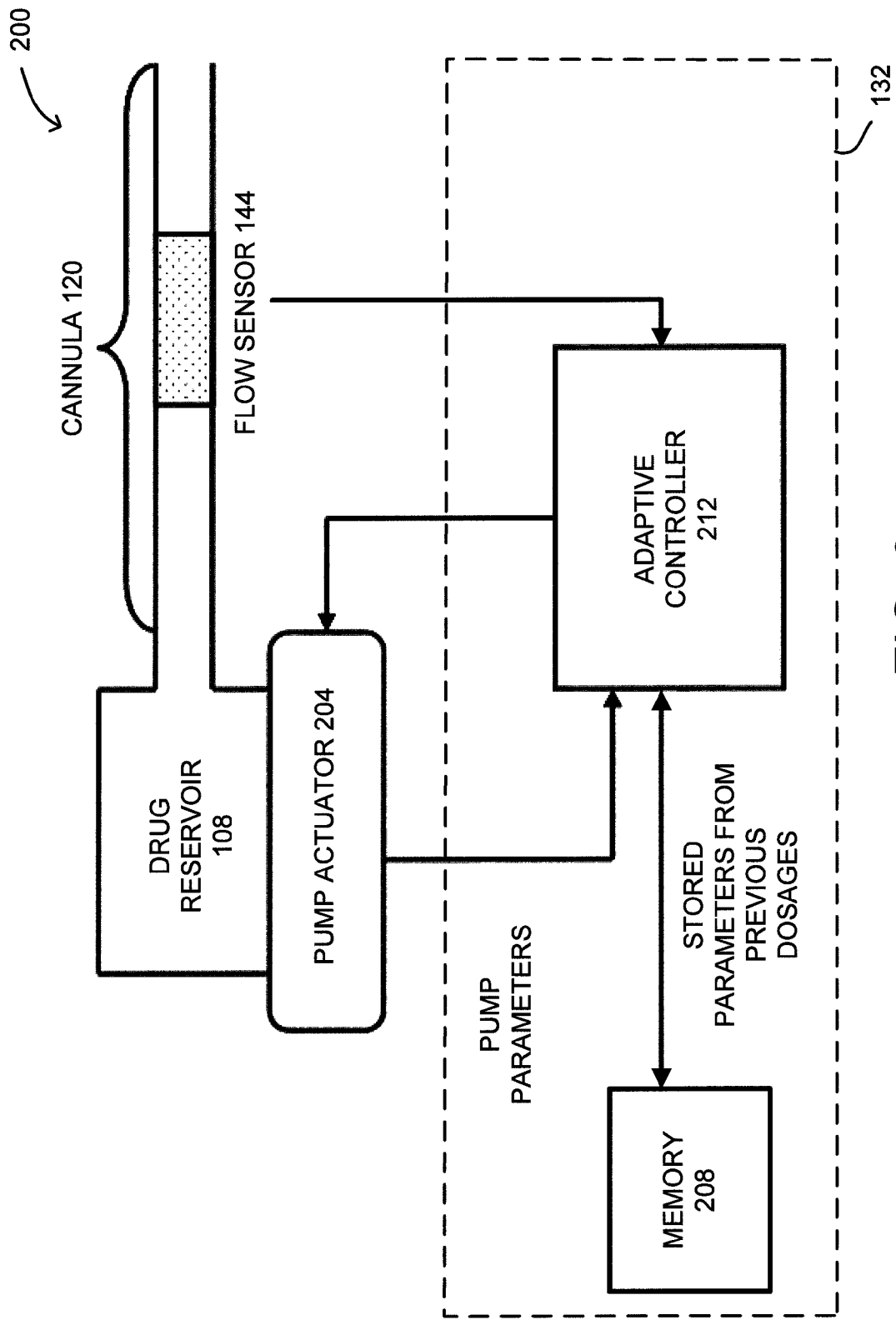
FIG. 3 is a block diagram of a drug-delivery pump in accordance with one embodiment of the invention.

FIG. 3 is a block diagram of a drug-delivery pump 200 that depicts the control circuitry 132 in greater detail. The drug-delivery pump 200 may be any type of external or internal pump having an actuator 204 that forces the liquid from the drug reservoir 108 into and through the cannula 120. For example, the drug-delivery pump 200 may be an electrolysis-driven pump and, with reference to FIGS. 1 and 2 described above, the pump actuator 204 may include the electrolyte chamber 112, the expandable diaphragm 124, and the electrolysis electrodes 134. For its part, the control circuitry 132 includes computer memory 208 for storing one or more conditions of the pump 200, and an adaptive controller 212 for controlling the pump actuator 204 based on a change in a condition of the pump 200. Optionally, the control circuitry 132 may also include one or more module(s) to convert raw data received from the flow sensor 144 into a meaningful value (e.g., into a flow rate in nL/min) and/or to convert similarly raw data received from the pump actuator 204 into a meaningful value. Alternatively, the functions performed by such module(s) may instead be performed by the adaptive controller 212.

The computer memory 208 may be implemented as any type of volatile or non-volatile (e.g., Flash) memory, while the adaptive controller 212 and/or the module(s) described above may each be implemented as any software program, hardware device, or combination thereof that is capable of providing the functionality described herein. For example, the adaptive controller 212 and/or the module(s) described above may each be an application-specific integrated circuit (ASIC) or a field-programmable gate array (FPGA). Alternatively, the adaptive controller 212 may be implemented using a general-purpose microprocessor (e.g., any of the PENTIUM microprocessors supplied by Intel Corp.) that is programmed using any suitable programming language or languages (e.g., C++, C#, Java, Visual Basic, LISP, BASIC, PERL, etc.). Suitable control programming is straightforwardly implemented by those of skill in the art without undue experimentation.

In one particular embodiment, as further described below, the control circuitry 132 is programmed to deliver a fixed dosage of the drug from the drug reservoir 108 to the target site at periodic time intervals, and is configured to store the conditions of the pump 200 at each of those time intervals in the computer memory 208. Some exemplary and non-limiting conditions internal to the pump 200 that may be stored at each dosing interval (or at other periodic intervals) include the current through, voltage across, or resistance of the electrolysis electrodes 134; the total electrical charge used to drive the electrolysis electrodes 134; the maximum flow rate of the drug through the cannula 120; any variations in flow patterns of the drug through the cannula 120; the actuation time required for the pump 200 to achieve a particular flow rate of the drug through the cannula 120; the time required for the flow of drug to ramp down from a particular flow rate to a flow rate of zero; the time delay between the initial actuation of the pump 200 and the initial flow of drug through the cannula 120; the efficiency of the pump actuator 204 (which, in the case of an electrolysis-driven pump 200, may be defined as the ratio between the amount of charge pumped through the actuator 204 and the amount of gas generated thereby); the internal pressure of the drug reservoir 108; the acceleration experienced by the pump 200; flow sensor parameters particular to the flow sensor 144 architecture (e.g., where the flow sensor 144 is a resistive temperature detector, the resistance of the sensor and heater elements may be stored); and the physical dimensions of the pump actuator 204, the drug reservoir 108, and/or the cannula 120, which may change due to blockages, scarring, or other biochemical/physiological events.

In one embodiment, these parameters are measured either directly or indirectly by using physical sensors, such as, for example, the flow sensor(s) 144, pressure sensors in the drug reservoir 108 or cannula 120, accelerometers, gyroscopes, altimeters, sensors in proximity to the electrolysis electrodes 134 (to measure, for example, their resistance, the current passing therethrough, and/or the voltage thereat or thereacross), or any other sensor dispersed throughout the pump 200. In other embodiments, these parameters are determined by using known relationships. For example, the flow rate of the drug through the cannula 120 may be determined by using a pressure sensor in the cannula 120 and by utilizing the well-known linear relationship between pressure and flow rate. In still other embodiments, many of these parameters may ascertained by analyzing the electrical waveforms used to drive the pump actuator 204, and/or by analyzing the flow profiles sensed by the flow sensor(s) 144.

In all cases, as further described below, the adaptive controller 212 of the control circuitry 132 can receive and process this parameter data and compensate for any change in a condition of the pump 200 in order to adjust its operation to maintain a target dosage level. This "self-compensation" may be achieved by storing, as mentioned above, parameter data from the pump 200 state at the time of the previous dosages and by considering real-time parameter values to determine the optimal actuation current for the electrolysis electrodes 134 and/or their actuation duration at the next dosing event. For example, as illustrated in FIG. 3, the adaptive controller 212 may receive, analyze, and process the stored parameters from previous doses, real-time data from the pump actuator 204, and real-time data from the flow sensor(s) 144 (e.g., flow rate data) to ascertain and direct appropriate output signals to the pump actuator 204 (i.e., in order to drive the pump 200 in the appropriate manner). For initial dosing, or in cases where the above-described data may be unavailable (e.g., due to a reset action in the pump 200), the adaptive controller 212 may employ a set of pre-defined reference parameter values. These reference values may be specific to the characteristics of the particular pump 200 employed, for example specific to the types of electrolysis electrodes 134 employed, the type of electrolytic solution used, and/or the physical dimensions of the pump actuator 204, drug reservoir 108, and cannula 120.

In one mode of operating an electrolysis-driven pump 200, the electrolysis electrodes 134 are driven using a constant current for a variable amount of time. In this mode, the constant current results in a monotonic rise in the flow rate of the drug through the cannula 120 until the current is shut off, at which point the residual pressure in the pump 200 gives rise to a slow decay in the flow rate until the flow rate reaches zero. In one functional example for this mode of operation, the following three parameters are stored in the computer memory 208 at each dosing interval: the current supplied to the electrolysis electrodes 134 in order to drive the pump 200 (I); the maximum flow rate of the drug through the cannula 120 ($F_{max}$); and the volume of liquid (i.e., drug) that is delivered by the pump 200, due to residual pressure, after the pump actuator 204 is deactivated ($V_{shutoff}$). This stored information is then used, in future doses, to improve the dosing speed and accuracy. For example, the current used to drive future doses may be adjusted based on previous dose data (e.g., increased if the maximum flow rate is too low, and decreased if the maximum flow rate is too high) in order to keep the duration of each dose, and the volume of the drug delivered on each dose, relatively consistent. In one embodiment, this is done in a linear fashion as follows:

$$I_{current} = F_{optimal}/F_{max,previous} \times I_{previous}$$

where $I_{current}$ is the current to be supplied to the electrolysis electrodes 134 during the current dose, $F_{optimal}$ is the desired maximum flow rate of the drug through the cannula 120, $F_{max,previous}$ was the maximum flow rate of the drug through the cannula 120 during the previous dose, and $I_{previous}$ was the current supplied to the electrolysis electrodes 134 during the previous dose.

As another example, the shut-off time of the pump actuator 204 may instead, or in addition, be adjusted (e.g., shut off later if the volume of the liquid delivered after the pump actuator 204 is deactivated is lower than expected, and shut off earlier if the volume of the liquid delivered after the pump actuator 204 is deactivated is higher than expected) in order to keep the volume of the drug delivered relatively consistent. Once again, this may be done using a linear approximation, where the pump actuator 204 is deactivated as soon as the following condition is met:

$$V_{accumulated} + F/F_{max,previous} \times V_{shutoff,previous} = V_{target}$$

where $V_{acuumulated}$ is the total volume of the drug delivered so far in the current dose, F is the real-time flow rate of the drug through the cannula 120, $F_{max,previous}$ was the maximum flow rate of the drug through the cannula 120 from the previous dose, $V_{shutoff,previous}$ was the volume of the drug delivered after the pump actuator 204 was shut off in the previous dose, and $V_{target}$ is the target volume of the drug to be delivered. In this manner, the adaptive controller 212 constantly adjusts the way in which the pump 200 is actuated, and accounts for systematic, non-random changes in the pump 200 characteristics.

Determining and controlling both the amount of current needed to initiate the flow of drug through the cannula 120 and then to reach a particular flow rate, as well as the amount of liquid delivered from the drug reservoir 108 after the current is no longer applied to the electrolysis electrodes 134, is of particular benefit when the pump 200 is an electrolysis-driven pump. In particular, the first parameter is important because the amount of current needed to initiate the flow of drug through the cannula 120 and to reach a particular flow rate depends on how much liquid is left in the drug reservoir 108. Using too low a current would be power-inefficient, since all systems would be running even though there would be no or very low flow of drug through the cannula 120. On the other hand, using too high a current could cause the flow rate of the drug to overshoot to unsafe levels. The second parameter is also of importance since the volume of drug delivered after the pump 200 is turned off is dependent primarily on the gas/liquid ratio in the electrolysis chamber 112. For doses later in the life-cycle of the pump 200 (e.g., where the pump 200 runs with a high gas/liquid ratio in the electrolysis chamber 112), there is much more gas that needs to be dissipated before the pump 200 can fully stop. The opposite is true for earlier doses.

As will be understood by one of ordinary skill in the art, in addition to the two examples given above, the adaptive controller 212 may recognize and analyze numerous other changes in conditions internal to the pump 200 when controlling the pump actuator 204 and, ultimately, the dispensing of the drug from the drug reservoir 108. For example, there may be situations where is it desirable for the pump 200 to reach an optimal flow rate ($F_{optimal}$) for each dose in a specified period of time ($t_{optimal}$) and to then maintain that flow rate for the remainder of the dose. One way to achieve this is to begin each dose by using a constant current ($I_{starting}$) to drive the electrolysis electrodes 134 of the pump 200 until the optimal flow rate ($F_{optimal}$) is reached, at which point feedback from the flow sensor 144 and an algorithm (e.g., a proportional-integral-derivative ("PID") algorithm or another algorithm) may be used to adjust the current supplied to the electrolysis electrodes 134 to maintain that optimal flow rate ($F_{optimal}$) for the remainder of the dose. In other words, the pump 200 may be driven using a time-varying current waveform. In one embodiment, in order to achieve the optimal flow rate ($F_{optimal}$) in the specified period of time ($t_{optimal}$), the starting current ($I_{starting}$) is adjusted from dose to dose. In a manner similar to before, this can be done, for example, using a linear approximation (although, as will be understood by one of ordinary skill in the art, non-linear approximations may also be employed for any of the parameters derived herein). More specifically, the starting current for the current dose ($I_{starting,current}$) can be calculated using the starting current from the previous dose ($I_{starting,previous}$) and the time it took for the flow rate to reach the optimal flow rate ($F_{optimal}$) in the previous dose ($t_{previous}$), as follows:

$$I_{starting,current} = t_{previous}/t_{optimal} \times I_{starting,previous}$$

Figure 4:
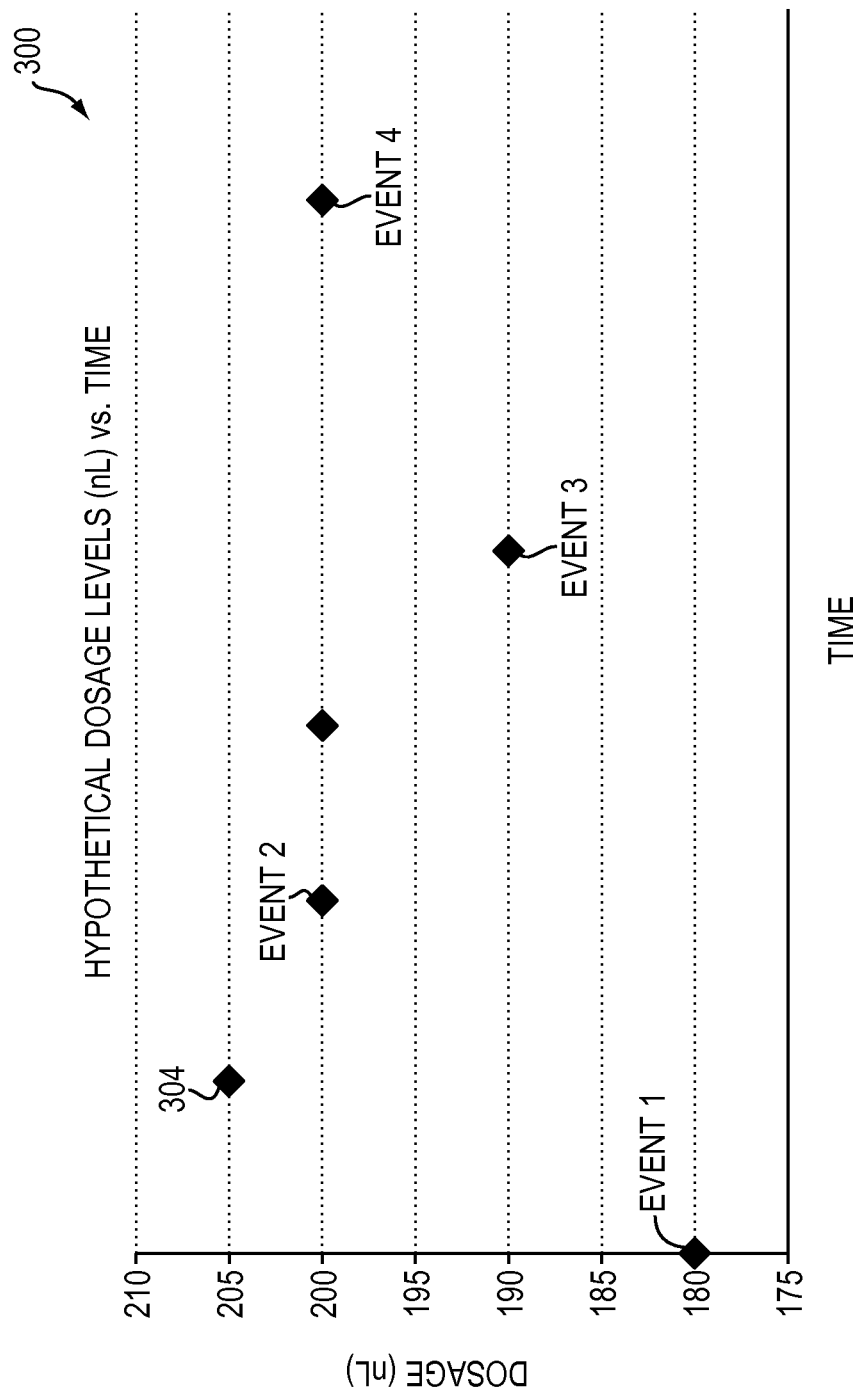
FIG. 4 is a graph representing an example of how each of the drug-delivery pumps depicted in FIGS. 1-3 may adapt to changing conditions within the pump to deliver a target dosage level.

Referring now to FIG. 4, an exemplary graph 300 illustrating the effects of the above-described adaptive control on the drug dosage level is depicted. In this example, the target dosage level to be delivered during each release event is 200 nanoliters (nL). Event 1 corresponds to an initial dosing of 180 nL based on calculations using the reference parameter values. The adaptive controller 212 then calculates appropriate adjustments to the pump 200 parameters (e.g., as described above, the amount of current supplied to the electrolysis electrodes 134 and/or the actuation time thereof may be increased in order to increase the volume of drug delivered to the target site) until a target delivery of 200 nL is achieved at Event 2. As illustrated, there may be a point 304 in time between Event 1 and Event 2 during which the adaptive controller 212 overcompensates and the pump 200 delivers more than the target dosage (e.g., 205 nL). In this case, the adaptive controller 212 refines its adjustments to the pump 200 parameters (e.g., as described above, the amount of current supplied to the electrolysis electrodes 134 and/or the actuation time thereof may be decreased in order to decrease the volume of drug delivered to the target site) until the target delivery of 200 nL is in fact achieved at Event 2.

Continuing with the example depicted in the graph 300 of FIG. 4, the dosage at Event 3 then drops to 190 nL due to a change in one or more of the pump 200 parameters. Exemplary conditions within the pump 200 itself that may change and lead to such a decrease in the dosage of the drug delivered (i.e., to a decrease in the efficiency of the pump 200) can include the degradation (e.g., erosion or corrosion) of the electrolysis electrodes 134, a decrease in the concentration of the electrolytes in the solution present in the electrolysis chamber 112, and/or general mechanical or chemical wear. In response, the adaptive controller 212 then compensates as described above so that the pump 200 releases the correct amount of drug at Event 4. The pump 200 thus dynamically reacts to changing conditions of the pump 200.

Figure 5A:
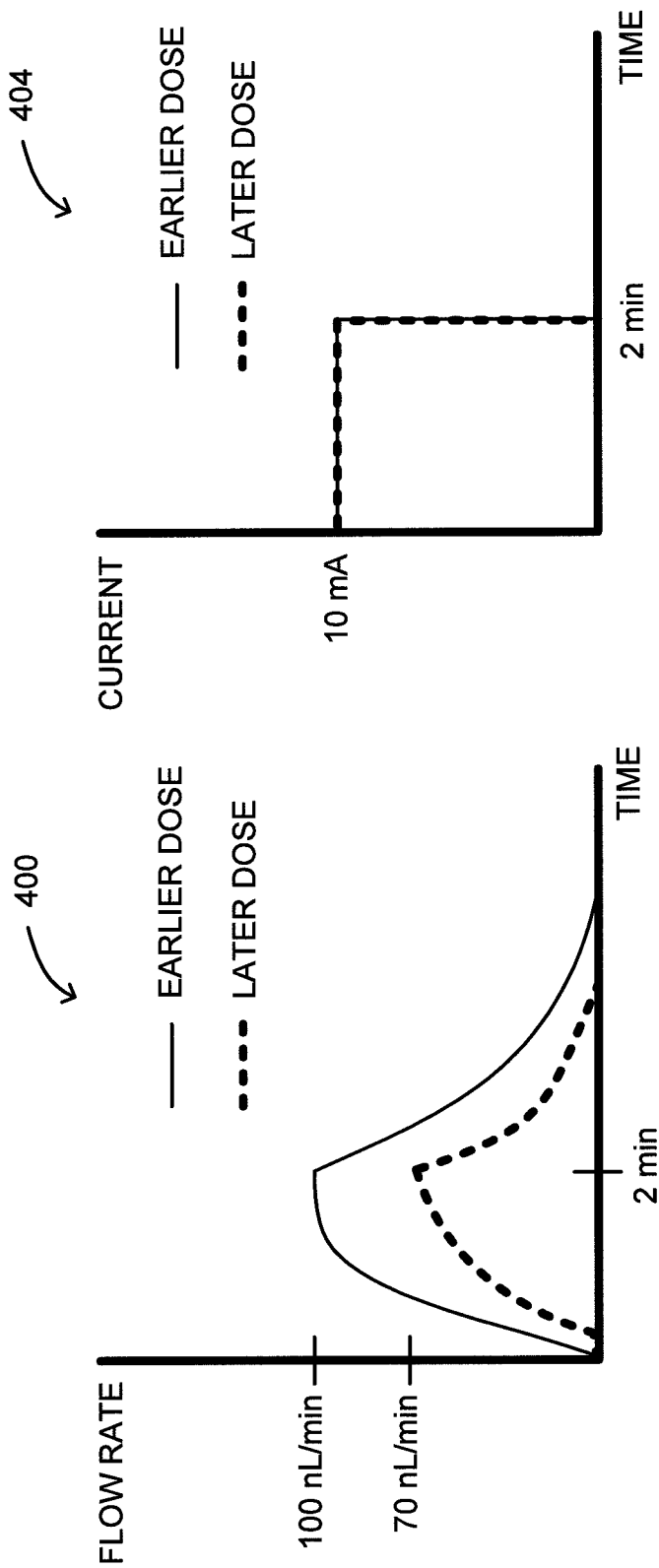
FIG. 5A illustrates exemplary flow and actuation profiles of a pump that operates without feedback control.

FIG. 5A depicts exemplary flow profiles 400 and actuation profiles 404 for a pump that operates without the feedback control provided by the control circuitry 132 (e.g., for a pump employing an open-loop control system). As shown, the amount of drug delivered at later times decreases even though the actuation current remains the same (the actuation profiles 404 for the earlier and later doses overlap in FIG. 5A), due to decreasing pump efficiency.

Figure 5B:
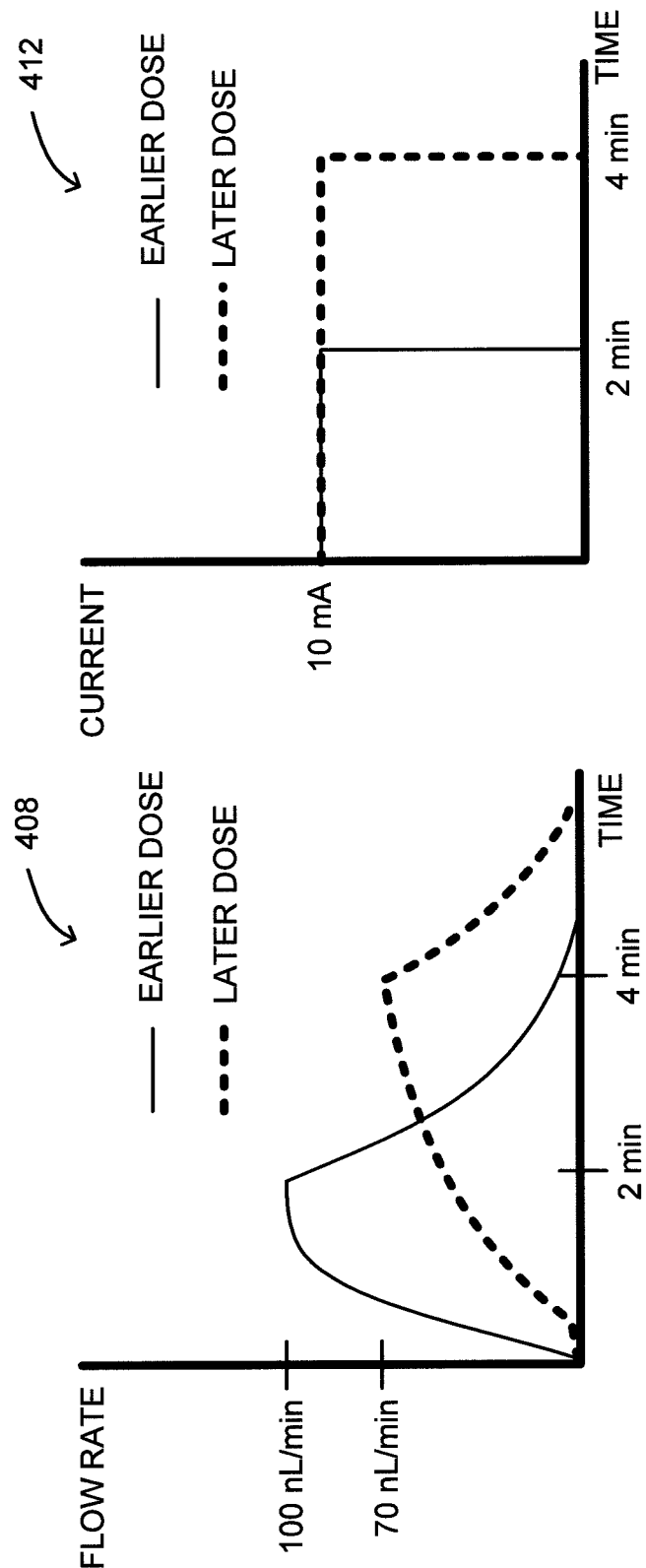
FIG. 5B illustrates exemplary flow and actuation profiles of a pump whose actuator is actuated for a longer period of time as the pump's efficiency decreases.

FIG. 5B depicts exemplary flow profiles 408 and actuation profiles 412 for a pump 200 that operates with the feedback control provided by the control circuitry 132. In particular, FIG. 5B shows how increasing the pumping time for a later dose can compensate for reduced pump 200 efficiency. More specifically, for the later dose, the pump 200 actuates for a longer period of time at the same current in order to successfully deliver the target dosage amount.

Figure 5C:
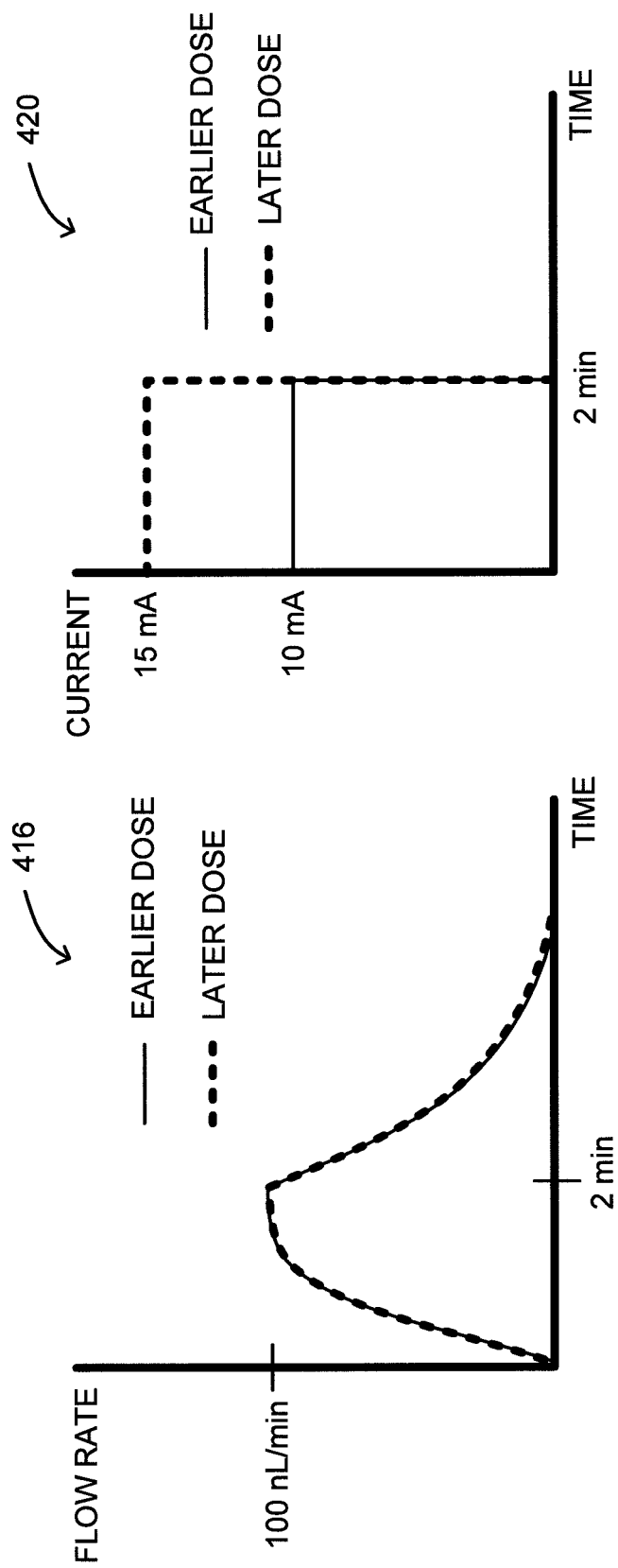
FIG. 5C illustrates exemplary flow and actuation profiles of a pump whose actuation current is increased as the pump's efficiency decreases.

FIG. 5C also depicts exemplary flow profiles 416 and actuation profiles 420 for a pump 200 that operates with the feedback control provided by the control circuitry 132. In particular, FIG. 5C shows how the dosing time for the earlier and later doses can be kept constant while still compensating for decreased pump 200 efficiency by increasing the actuation current of the later dose. The flow profiles 416 for the earlier and later doses overlap, illustrating that the same amount of drug is delivered during both dosages.

C. Adaptive Control Based Upon Conditions of the Target Site

In other embodiments, with reference again to FIGS. 1-3, the adaptive controller 212 can also receive information from the target site sensor(s) 148 that monitor the drug-delivery treatment area, and thereafter change the target dosage for certain time periods. More particularly, if changes in the treatment area (e.g., worsening or improvement of symptoms, changes in biological or biochemical parameters, changes in electrical activity, changes in pressure, etc.) require a higher or lower dosing level or a change in the frequency of dosages, the adaptive controller 212 can control the pump actuator 204 so as to adjust the dosage and maintain it at a new level until another change is required. In other words, the adaptive controller 212 may actuate the pump 200 to achieve a desired result, such as the regulation of a specific physiological state or biochemical parameter. As before, the parameters sensed by the target sensor(s) 148 (e.g., pressure, temperature, etc.) may be stored in the computer memory 208 for later use (e.g., for comparison in determining the appropriate dosage of drug to be delivered).

As an example, assume that the pump 200 delivers an initial target dosage of 200 nL every 30 minutes. After a period of time, either due to a change in the treatment area or dosing regimen, the dosage may need to be decreased to 150 nL. The adaptive controller 212 may then operate the pump actuator 204 so as to deliver 150 nL of the drug every 30 minutes until instructed otherwise, either by another change in the treatment area or by a user of the pump 200.

Advantageously, this flexibility facilitates the use of the pump 200 with a wide range of treatment regimens that may require the staggering of different dosages or dosage frequencies over prolonged periods of time.

Optionally, the adaptive controller 212 may be programmed to respond to both a change in a condition of the pump 200 itself and, at the same time, to a change in condition of the target treatment area. In other words, the adaptive controller 212 may receive data from both sensors or other devices internal to the pump 200 and from the target site sensor(s) 148, analyze both sets of data, and control the pump actuator 204 to account for both sets of data. Alternatively, in another embodiment, if the deterministic parameters are to be those of the pump 200 itself rather than those of the treatment area, the adaptive controller 212 may be programmed to refrain from initiating actions based on, for example, blockages that may form within the target area due to physiological changes or scarring.

D. Exemplary Uses of the Dynamic, Adaptively Controlled Drug-Delivery Pumps

Figure 6:
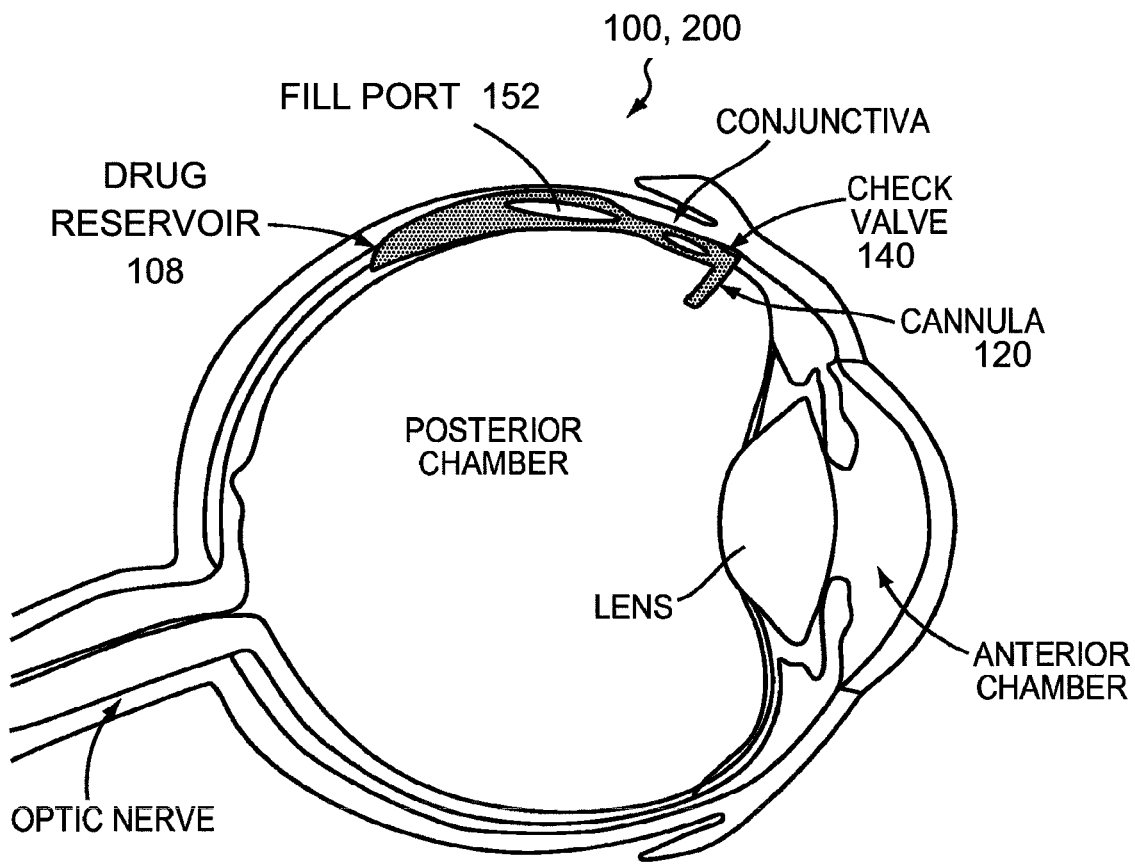
FIG. 6 is a sectional view of a patient's eye illustrating implantation therein of a drug-delivery pump in accordance with one embodiment of the invention.

FIG. 6 schematically illustrates a drug-delivery pump 100, 200 implanted in the eye of a patient in accordance with one embodiment of the invention. As illustrated, the pump 100, 200 is placed upon the conjunctiva of the eye, and a distal end of the cannula 120 is inserted therethrough in to the posterior chamber of the eye. As such, the distal end of the cannula 120 (and, hence, the drug reservoir 108) is in fluid communication with the patient. The drug-delivery pump 100, 200 then administers a therapeutic liquid to the posterior chamber of the eye through the cannula 120 and the check valve 140, which, as previously mentioned, may be employed to prevent the backflow of the liquid. In particular, the pump actuator 204 may be controlled through use of the adaptive controller 212 and the other control circuitry 132 in any of the manners described hereinabove (e.g., based on a change in a condition of the pump itself and/or based on conditions of the target site) so as to deliver one or more dosages of the liquid from the drug reservoir 108, through the cannula 120, and into the patient's eye.

In other embodiments, the pump 100, 200 is used to administer the liquid to the anterior chamber of the eye, which is separated from the posterior chamber by the lens. More generally, however, the pump 100, 200 may, as previously mentioned, be employed to administer liquid to any portion of the patient's body.

As an additional example, the pump 100, 200 may be a body-adhered electrolysis-driven pump for the infusion of medication into a patient's subcutaneous tissue. For example, the pump 100, 200 may continuously deliver insulin to the patient's body over three to seven days. A patient may need, however, to recalculate his or her insulin delivery (e.g., increase or decrease basal rates over time), as well as program the pump 100, 200 to give an intermittent bolus spike of insulin after a meal. Accordingly, the pump 100, 200 in this example can adapt the electrolysis to increase or decrease the flow of insulin to accurately deliver the correct fluidic volumes over time. Furthermore, infusion of a drug over an extended period of time, such as three days, may subject the pump 100, 200 to new environmental conditions. For example, a patient may drive from low to high altitudes or fly in a pressurized plane. The pump 100, 200 can use both environmental signals (e.g., altimeter, pressure change, flow rate change, etc.) to adjust the flow of the drug and to ensure the accurate delivery of the drug.

As yet another example, the pump 100, 200 may use input from an accelerometer or gyroscope in order to sense a patient's position. For example, the pump 100, 200 may sense that the patient was horizontal during the hours of 10 pm to 6 am for the previous 7 days (because, for example, the patient was sleeping). In this case, the pump 100, 200 may then recognize the patient's sleep time (i.e., from sensing the patient to be in a horizontal position) or REM sleep cycle and then use that information to infuse a different volume of drug (or drug at specific times) to accommodate optimal conditions. For example, the flow rate of the pump 100, 200 may be adjusted to an amount pre-prescribed by a physician for infusion during sleep (e.g., it is often best to inject some glaucoma medications to a patient's eye during REM sleep cycle in order to better distribute the medication throughout the eye, while some medications such as Anti-VEGF drugs for the retina act over a period of a month and should be injected calmly into the vitreous; in addition, a lower basal rate of insulin or less pain medication may be injected during sleep). In contrast to understanding when a patient is sleeping, the pump 100, 200 may also recognize when the patient is exercising or when the patient is not supine, and adjust its infusion of drug accordingly (e.g., such as to that which is pre-programmed by the physician for infusion during certain activities).

Advantageously, the control circuitry 132 described herein can be employed for pumps that are not uniform in their characteristics, either due to user-selected preferences or variations arising during the manufacturing process. The types of electrodes and electrolytic solution used, for example, determine the performance of electrolysis-driven pumps. The control circuitry 132 is, however, robust and versatile enough to accommodate pumps that operate across a wide range of parameter values. As another example, manufacturing process variations in the resistance of the flow sensor elements can be mitigated by the adaptive nature of the control circuitry 132. More specifically, mismatched resistances in the flow sensor elements resulting from the process variations will result in an offset for which the control circuitry 132 can compensate.

Optionally, the control circuitry 132 may also serve to enhance safety and efficacy of the pump 100, 200 by monitoring certain key pump parameters. For example, acceptable ranges may be defined for each parameter or for some overall combination of parameters corresponding to a specific pump state, during which the pump 100, 200 continues to operate normally. Should an individual parameter or some combination of parameters not fall within these pre-defined ranges, an action may then be triggered within the pump 100, 200, such as shutting off or alerting the user that a response is required. For example, the pump 100, 200 may alter a patient by illumination, sound, vibration, or shock. In one embodiment, the alert is programmed to occur when the patient is moving to maximize the likelihood that the patient will receive the alert and also to conserve battery power by avoiding alerts while the patient is sleeping.

In one particular example, the control circuitry 132 can respond to and predict the failure of a flow sensor 144. Where, for example, the flow sensor 144 includes a group of heaters and resistive temperature detectors, one of its elements may begin to fail after an indeterminate number of doses due to thermal stresses experienced during its use. The control circuitry 132 can monitor the resistance of the heater elements periodically (e.g., from dose to dose) and detect changes in resistance that may indicate the start of failure or outright failure (such as an open-circuit). Other pump components including sensors and actuators that employ resistive or capacitive elements can likewise be monitored by the control circuitry 132 to ensure proper functional operation.

Having described certain embodiments of the invention, it will be apparent to those of ordinary skill in the art that other embodiments incorporating the concepts disclosed herein may be used without departing from the spirit and scope of the invention. For example, although the adaptive controller 212 and the other control circuitry 132 has primarily been described for use in connection with an electrolysis-driven pump, this is for illustrative purposes only. Those of ordinary skill in the art will readily appreciate and understand that the adaptive controller 212 and the other control circuitry 132 may also be usefully employed in other types of drug-delivery pumps, such as those that rely on, for example, electroosmosis, mechanical actuation, or pressure-driven mechanisms. Accordingly, the described embodiments are to be considered in all respects as only illustrative and not restrictive.

What is claimed is:

1. A method of delivering a drug to a patient from drug-delivery pump comprising a drug reservoir, a cannula, and a pump actuator for forcing a liquid drug from the drug reservoir into the patient via the cannula at period time intervals, the method comprising:

establishing fluid communication between the drug reservoir and the patient;

measuring at least one quantitative electrical or flow pump operating parameter;

storing (i) a fixed dosage of the liquid drug to be delivered by the pump actuator through the cannula during each of a plurality of dosing intervals and (ii) a value of the at least one quantitative pump operating parameter measured during a previous dosing interval, the pump actuator being operative during the previous dosing interval to deliver the fixed dosage; and controlling the pump actuator by computing actuator settings based at least in part on the stored fixed dosage and a change in a condition of the pump actuator specified by a quantitative difference between the stored value of the pump operating parameter and a current value of the pump operating parameter, and adjusting the pump actuator in accordance with the computed actuator settings to thereby compensate for the change in actuation time required for the drug-delivery pump to achieve a target flow rate of the liquid drug through the cannula or a time required for the flow of the liquid drug to decrease from the target flow rate to a flow rate of zero;

wherein the drug-delivery pump is an electrolysis-driven pump and the pump actuator comprises electrolysis electrodes driven by a current, and wherein the controlling the pump actuator comprises varying actuation current supplied to the electrolysis electrodes.

2. The method of claim 1, wherein controlling the pump actuator comprises maintaining delivery of a substantially fixed dosage of the liquid at the periodic time intervals to the patient.

3. The method of claim 2 further comprising storing conditions of the pump actuator at each time interval.

4. The method of claim 1 further comprising measuring a flow rate of the liquid drug into the patient.

5. The method of claim 4, wherein controlling the pump actuator comprises analyzing at least one of the flow rate, stored conditions of the pump actuator from previous dosing interval, or real-time data from the pump actuator.

6. The method of claim 1, wherein controlling the drug-delivery pump comprises varying an actuation duration of the electrolysis electrodes.

7. The method of claim 1, wherein controlling the drug-delivery pump comprises driving the electrolysis electrodes with a constant current.

8. The method of claim 1, wherein controlling the drug-delivery pump comprises driving the electrolysis electrodes with a time-varying current waveform.

9. The method of claim 1, wherein controlling the pump actuator comprises maintaining delivery of a substantially fixed dosage of the liquid drug over time through continuous infusion to the patient.

\* \* \* \* \*